United States Patent
Bissantz et al.

(10) Patent No.: US 8,664,216 B2
(45) Date of Patent: Mar. 4, 2014

(54) SPIRO-5,6-DIHYDRO-4H-2,3,5,10B-TETRAAZA-BENZO[E]AZULENES

(75) Inventors: Caterina Bissantz, Village-Neuf (FR); Erwin Goetschi, Reinach BL (CH); Roland Jakob-Roetne, Inzlingen (DE); Raffaello Masciadri, Muenchenstein (CH); Emmanuel Pinard, Linsdorf (FR); Hasane Ratni, Habsheim (FR); Mark Rogers-Evans, Bottmingen (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 807 days.

(21) Appl. No.: 12/613,554

(22) Filed: Nov. 6, 2009

(65) Prior Publication Data
US 2010/0120751 A1    May 13, 2010

(30) Foreign Application Priority Data
Nov. 13, 2008  (EP) .................... 08169028

(51) Int. Cl.
*A61P 9/00* (2006.01)
*A61K 31/55* (2006.01)
*C07D 487/12* (2006.01)

(52) U.S. Cl.
USPC ........................ 514/220; 540/563; 540/564

(58) Field of Classification Search
USPC ................... 514/220; 540/563, 564
See application file for complete search history.

(56) References Cited

U.S. PATENT DOCUMENTS

| | | |
|---|---|---|
| 7,265,104 B2 | 9/2007 | Elliott et al. |
| 2002/0103373 A1 | 8/2002 | Hockstra et al. |
| 2011/0245237 A1 | 10/2011 | Dolente et al. |
| 2011/0251183 A1 | 10/2011 | Dolente et al. |
| 2011/0263573 A1 | 10/2011 | Dolente et al. |
| 2011/0263578 A1 | 10/2011 | Dolente et al. |
| 2011/0275801 A1 | 11/2011 | Dolente et al. |

FOREIGN PATENT DOCUMENTS

| | | |
|---|---|---|
| CA | 2550868 | 3/2012 |
| EP | 2292621 | 3/2011 |
| KR | 2007/0020462 | 2/2007 |
| WO | 96/22292 | 7/1996 |
| WO | 99/06409 | 2/1999 |
| WO | 02/083681 | 10/2002 |
| WO | 2004/074291 | 9/2004 |
| WO | 2005/068466 | 7/2005 |
| WO | 2006021882 | 3/2006 |
| WO | 2006/114706 | 11/2006 |
| WO | 2006123242 | 11/2006 |
| WO | 2008084005 | 7/2008 |
| WO | 2010/057795 | 5/2010 |

OTHER PUBLICATIONS

Robben et al., Am. J. Physiol. Renal Physiol, vol. 291 pp. F257-270 (2006).
Neumann, J. Neuroendocrinal. vol. 20, pp. 858-865 (2008).
Ebner et al., Eur. J. Neurosci. vol. 15, pp. 384-388 (2002).
Kendler et al., Arch. Gen. Psychiatry vol. 60, pp. 789-796 (2003).
Regier et al., Br. J. Psychiatry Suppl. pp. 24-28 (1998).
Bielsky et al., Neuropsychopharmacology vol. 29, pp. 483-493 (2004).
Liebsch et al., Regul. Pept. vol. 59 pp. 229-239 (1995).
Yirmiya et al., vol. 11, pp. 488-494 (2006).
Thompson et al., Psychoneuroendocrinology vol. 29, pp. 25-48 (2004).
Raskind et al., Biol. Psychiatry vol. 22 pp. 453-462 (1987).
Altemus et al., Arch. Gen. Psychiatry vol. 49, pp. 9-20 (1992).
Michelini & Morris, Ann. N. Y. Acad. Sci. vol. 897, pp. 198-211 (1999).
Van Kerckhoven et al., Eur. J. Pharmacol. vol. 449, pp. 135-141 (2002).
Brouard et al., Bjog, vol. 107 pp. 614-619 (2000).
Aughton et al., Br. J. Pharmacol. p. 253 (2008).
Gupta et al, Br. J. Pharmacol. vol. 155, pp. 118-126 (2008).
Gal, et al., Progress in Brain Research, Elsevier, vol. 139, pp. 197-210, XR001205440 (2002).

(Continued)

*Primary Examiner* — Brenda Coleman

(57) ABSTRACT

The present invention is concerned with spiro-dihydrotetraazabenzoazulenes, i.e. spiro-5,6-dihydro-4H-2,3,5,10b-tetraaza-benzo[e]azulenes of formula I

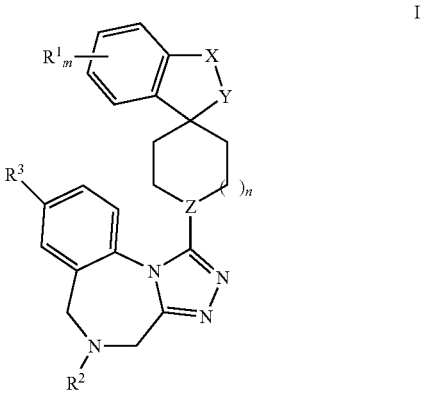

wherein $R^1$, $R^2$, $R^3$, X, Y, Z, m and n are as described herein. The compounds according to the invention act as V1a receptor modulators and are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

22 Claims, No Drawings

(56) References Cited

OTHER PUBLICATIONS

The English translation of the Japanese Office Action, issued on Aug. 6, 2013, in the corresponding Japanese application No. 2011-535965., pp. 5.
(International Search Report for PCT/EP2011/057368 Jul. 14, 2011).
(International Search Report for PCT/EP2009/064804 Jan. 14, 2010).
(International Search Report PCT/EP2011/056391 Jun. 27, 2011).
(International Search Report PCT/EP2011/056071 May 12, 2011).
(International Search Report for PCT/EP2011/054582 Mar. 25, 2011).
(International Search Report PCT/EP2009/065354 Feb. 8, 2010).
(International Search Report PCT/EP2011/055516 May 23, 2011).
The English translation of the Russian Decision on Granting a Patent, dated Dec. 4, 2013, in the corresponding Russian Patent Application No. 2011121049.

SPIRO-5,6-DIHYDRO-4H-2,3,5,10B-TETRAAZA-BENZO[E]AZULENES

PRIORITY TO RELATED APPLICATION(S)

This application claims the benefit of European Patent Application No. 08169028.1, filed Nov. 13, 2008, which is hereby incorporated by reference in its entirety.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviours in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8, "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al, (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhoea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

SUMMARY OF THE INVENTION

The present invention provides spiro-dihydrotetraazabenzoazulenes, i.e. spiro-5,6-dihydro-4H-2,3,5,10b-tetraazabenzo[e]azulenes, which act as V1a receptor modulators, and in particular as V1a receptor antagonists, their manufacture, and pharmaceutical compositions containing them.

The compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. The invention also provides such methods of treatment.

In particular, the present invention provides spiro-dihydrotetraazabenzoazulenes of formula I wherein X—Y is C(R$^a$R$^b$)—O, wherein R$^a$ and R$^b$ are each independently H or C$_{1-4}$-alkyl,
C(R$^c$R$^d$)—S(O)$_p$, wherein R$^c$ and R$^d$ are each independently H or C$_{1-4}$-alkyl,
C(O)O,
CH$_2$OCH$_2$, or
CH$_2$CH$_2$O, Z is CH or N;

R$^1$ is halo, cyano, C$_{1-4}$-alkoxy, or C$_{1-4}$-alkyl,

R$^2$ is H,
C$_{1-12}$-alkyl that is unsubstituted or substituted with one or more OH, halo, cyano or C$_{1-12}$-alkoxy,
—(CH$_2$)$_q$—R$^e$, wherein R$^e$ is phenyl or 5- or 6-membered heteroaryl, each unsubstituted or substituted with one or more substituent independently selected from A,
—(CH$_2$)$_r$NR$^i$R$^{ii}$,
—C(O)—C$_{1-12}$-alkyl, wherein C$_{1-12}$-alkyl is unsubstituted or substituted with one or more OH, halo, cyano or C$_{1-12}$-alkoxy,
—C(O)(CH$_2$)$_q$OC(O)—C$_{1-12}$-alkyl,
—C(O)(CH$_2$)$_q$NR$^i$R$^{ii}$,
—C(O)O—C$_{1-12}$-alkyl, wherein alkyl is unsubstituted or substituted with one or more OH, halo, cyano or C$_{1-12}$-alkoxy,
—S(O)$_2$—C$_{1-12}$-alkyl, or
—S(O)$_2$NR$^i$R$^{ii}$, R$^i$ and R$^{ii}$ are each independently H or C$_{1-12}$-alkyl, or together with the nitrogen atom to which they are bound form a 3- to 7-membered heterocycloalkyl containing one or two heteroatoms selected from N, O and S, which heterocycloalkyl is unsubstituted or substituted by one or more substituents independently selected from B, A is halo, cyano, OH, C$_{1-7}$-alkyl, halo-C$_{1-7}$-alkyl, or C$_{1-7}$-alkoxy, B is oxo, halo, OH, C$_{1-7}$-alkyl or C$_{1-7}$-alkoxy, R$^3$ is Cl or F, n is 1 or 2, m is 0, 1, 2, 3 or 4, p is 0, 1 or 2, q is 1, 2, 3 or 4, and r is 2, 3 or 4, or a pharmaceutically acceptable salt thereof.

DETAILED DESCRIPTION OF THE INVENTION

The present invention provides compounds which act as V1a receptor modulators, and in particular as V1a receptor antagonists. The invention further provides selective inhibitors of the V1a receptor since it is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. The preferred indications with regard to the present invention are the treatment of anxiety, depressive disorders, obsessive compulsive disorder, autistic spectrum disorders, schizophrenia, and aggressive behavior.

The V1a activity can be detected as described in the pharmacological test section.

The following definitions of the general terms used in the present description apply irrespective of whether the terms in question appear alone or in combination.

As used herein, the term "alkyl" denotes a saturated, i.e. aliphatic, hydrocarbon group including a straight or branched carbon chains. If not further specified, "alkyl" groups denote groups with 1 to 12 carbon atoms, like "C$_{1-12}$-alkyl". "C$_{1-4}$-alkyl" denotes alkyl groups with 1 to 4 carbon atoms and "C$_{1-7}$-alkyl" denotes alkyl groups with 1 to 7 carbon atoms. Examples for "alkyl" are methyl, ethyl, propyl, isopropyl(i-propyl), n-butyl, iso-butyl, sec-butyl, tert-butyl and the like. Preferred are methyl, ethyl and isopropyl.

The term "alkoxy" denotes a group —O—R' wherein R' is alkyl as defined above. "C$_{1-12}$-alkoxy" denotes alkoxy groups with 1 to 12 carbon atoms and "C$_{1-4}$-alkoxy" denotes alkoxy groups with 1 to 4 carbon atoms and "C$_{1-7}$-alkoxy" denotes alkoxy groups with 1 to 7 carbon atoms. Examples for "alkoxy" are methoxy, ethoxy, propoxy, tert-butoxy and the like. Preferred are methoxy and tert-butoxy.

The term "aromatic" means the presence of an electron sextet in a ring, according to Hückel's rule.

The term "cyano" denotes the group —CN.

The term "halo" or "halogen" denotes chloro, iodo, fluoro and bromo.

The term "halo-C$_{1-7}$-alkyl" or "C$_{1-7}$-haloalkyl" denotes a C$_{1-7}$-alkyl group as defined above wherein at least one of the hydrogen atoms of the alkyl group is replaced by a halogen atom, preferably fluoro or chloro, most preferably fluoro. Examples of halo-C$_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-C$_{1-7}$-alkyl groups are difluoro- or trifluoro-methyl or -ethyl.

The term "heterocycloalkyl" as defined herein refers to a monovalent 3 to 7 membered saturated ring containing one or two heteroatoms selected from N, O and S. Examples for heterocyclocalkyl moieties are tetrahydropyranyl, tetrahydropyranyl, pyrrolidinyl, morpholinyl, thiomorpholinyl, piperidinyl, or piperazinyl. Heterocycloalkyl is optionally substituted as described herein.

The terms "heteroaryl" and "5- or 6-membered heteroaryl" refer to a monovalent aromatic 5- or 6-membered monocyclic ring containing one or two ring heteroatoms selected from N, O, and S, the remaining ring atoms being C. 6-Membered heteroaryl are preferred. Examples for heteroaryl moieties include but are not limited to pyridinyl, pyrimidinyl, or pyrazinyl. Preferred is pyridinyl.

The term "oxo" when referring to substituents on heterocycloalkyl means that an oxygen atom is attached to the heterocycloalkyl ring. Thereby, the "oxo" can either replace two hydrogen atoms on a carbon atom or be attached to sulfur, so that the sulfur exists in oxidized form, i.e. bearing one or two oxygens. Preferable group where "oxo" is attached to sulfur is a group —SO$_2$.

When indicating the number of substituents, the term "one or more" means from one substituent to the highest possible number of substitution, i.e. replacement of one hydrogen up to replacement of all hydrogens by substituents. Thereby, one, two or three substituents are preferred. Even more preferred are one or two substituents or one substituent.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like. Preferred is the hydrochloric acid salt.

"Therapeutically effective amount" means an amount that is effective to prevent, alleviate or ameliorate symptoms of disease or prolong the survival of the subject being treated.

In detail, the present invention provides compounds of formula (I)

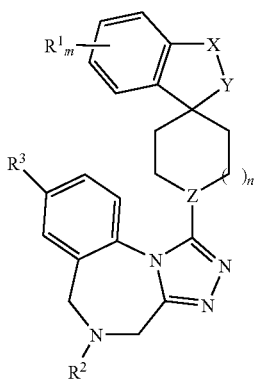

I wherein
X—Y is C(R$^a$R$^b$)—O, wherein R$^a$ and R$^b$ are each independently H or C$_{1-4}$-alkyl,
  C(R$^c$R$^d$)—S(O)$_p$, wherein R$^c$ and R$^d$ are each independently H or C$_{1-4}$-alkyl,
  C(O)O,
  CH$_2$OCH$_2$, or
  CH$_2$CH$_2$O,
Z is CH or N;
R$^1$ is halo, cyano, C$_{1-4}$-alkoxy, or C$_{1-4}$-alkyl,
R$^2$ is H,
  C$_{1-12}$-alkyl, unsubstituted or substituted with one or more OH, halo, cyano or C$_{1-12}$-alkoxy,
  —(CH$_2$)$_q$—R$^e$, wherein R$^e$ is phenyl or 5- or 6-membered heteroaryl, each unsubstituted or substituted with one or more substituents independently selected from A,
  —(CH$_2$)$_r$NR$^i$R$^{ii}$,
  —C(O)—C$_{1-12}$-alkyl, wherein C$_{1-12}$-alkyl is unsubstituted or substituted with one or more OH, halo, cyano or C$_{1-12}$-alkoxy,
  —C(O)(CH$_2$)$_q$OC(O)—C$_{1-12}$-alkyl,
  —C(O)(CH$_2$)$_q$NR$^i$R$^{ii}$, —C(O)O—C$_{1-12}$-alkyl, wherein alkyl is unsubstituted or substituted with one or more OH, halo, cyano or C$_{1-12}$-alkoxy,
  —S(O)$_2$—C$_{1-12}$-alkyl, or
  —S(O)$_2$NR$^i$R$^{ii}$,
R$^i$ and R$^{ii}$ are each independently H or C$_{1-12}$-alkyl, or together with the nitrogen atom to which they are bound form a 3- to 7-membered heterocycloalkyl containing one or two heteroatoms selected from N, O and S, which heterocycloalkyl is unsubstituted or substituted by one or more substituents independently selected from B,
A is halo, cyano, OH, C$_{1-7}$-alkyl, halo-C$_{1-7}$-alkyl, or C$_{1-7}$-alkoxy,
B is oxo, halo, OH, C$_{1-7}$-alkyl or C$_{1-7}$-alkoxy,
R$^3$ is Cl or F,
n is 1 or 2,
m is 0, 1, 2, 3 or 4,
p is 0, 1 or 2,
q is 1, 2, 3 or 4, preferably 1, and
r is 2, 3 or 4,
or a pharmaceutically acceptable salt thereof.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| brine | saturated sodium chloride solution in water |
| EDTA | ethylendiamin-tetraacetate |
| HEPES | 4-(2-hydroxyethyl)-1-piperazineethanesulfonic acid |
| HPLC | high performance liquid chromatography |
| Lawesson's reagent | 2,4-bis(4-methoxyphenyl)-1,3,2,4-dithiadiphosphetane-2,4-disulfide |
| MS | mass spectroscopy |
| NMR | nuclear magnetic resonance |
| RNA | ribonucleic acid |
| RT | room temperature |
| RT-PCR | reverse-transcriptase polymerase chain reaction |
| Tris | aluminium-tris(8-hydroxychinolin) |

The invention also provides pharmaceutical compositions, methods of using, and methods of preparing the aforementioned compounds.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the spirocyclic head group (HG) of the compounds of formula I, namely

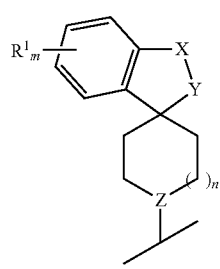

HG wherein at least the spiroatom as well as Z being CH are asymmetric carbon atoms. It is to be understood that present invention includes all individual enantiomers of head groups and mixtures of the respective enantiomers.

It is further understood that all embodiments of the invention as described below can be combined with each other.

In certain embodiments, X—Y is as described above, i.e. X—Y is
C($R^a R^b$)—O, wherein $R^a$ and $R^b$ are each independently H or $C_{1-4}$-alkyl,
C($R^c R^d$)—S(O)$_p$, wherein $R^c$ and $R^d$ are each independently H or $C_{1-4}$-alkyl, and p is 0, 1 or 2,
C(O)O,
CH$_2$OCH$_2$, or
CH$_2$CH$_2$O.

In certain embodiments, $R^a$ and $R^b$ are each independently H or methyl; in certain embodiments, $R^a$ is H and $R^b$ is H or methyl.

In certain embodiments $R^c$ and $R^d$ are each independently H or methyl; in certain embodiments, $R^c$ is H and $R^d$ is H or methyl; in certain embodiments, $R^c$ and $R^d$ are H. Thereby, p is 0, 1 or 2, preferably 0 or 2.

In certain embodiments, n is 1.
In certain embodiments, n is 2.
In certain embodiments, Z is as described above, i.e. CH or N.
In certain embodiments, Z is CH.
In certain embodiments, Z is N.
In certain embodiments, $R^1$ is as described above, i.e. halo, cyano, $C_{1-7}$-alkoxy, or $C_{1-7}$-alkyl. In certain embodiments, $R^1$ is halo, cyano, methoxy or methyl. In certain embodiments, $R^1$ is halo.

In certain embodiments, $R^1$ is F or Cl, preferably F. Thereby, m is 0, 1, 2, 3 or 4; preferably 0 or 1.
In certain embodiments, $R^1$ is halo.
In certain embodiments, $R^1$ is F.
In certain embodiments, m is 0.
In certain embodiments, m is 1.
In certain embodiments, X—Y is C($R^a R^b$)—O, wherein $R^a$ and $R^b$ are each independently H or methyl; CH$_2$—S(O)$_p$, wherein p is 0 or 2; C(O)O; CH$_2$OCH$_2$, or CH$_2$CH$_2$O; Z is CH or N and n is 1 or 2.
In certain embodiments, X—Y is C($R^a R^b$)—O, wherein $R^a$ and $R^b$ are each independently H or methyl; CH$_2$—S(O)$_p$, wherein p is 0 or 2; C(O)O; CH$_2$OCH$_2$, or CH$_2$CH$_2$O.
In certain embodiments, X—Y is C(H,Me)—O, CH$_2$—O, CH$_2$—S(O)$_2$, CH$_2$—S, C(O)O; CH$_2$OCH$_2$, or CH$_2$CH$_2$O.
In certain embodiments, X—Y is CH$_2$—O—, C(H,Me)—O—, or CH$_2$OCH$_2$.
In certain embodiments, X—Y is C($R^a R^b$)—O, wherein $R^a$ and $R^b$ are each independently H or methyl.
In certain embodiments, X—Y is C(H,methyl)-O.
In certain embodiments, X—Y is CH$_2$—O.
In certain embodiments, X—Y is CH$_2$—S(O)$_p$, wherein p is 0 or 2.
In certain embodiments, X—Y is CH$_2$—S(O)$_2$.
In certain embodiments, X—Y is CH$_2$—S.
In certain embodiments, X—Y is C(O)O.
In certain embodiments, X—Y is CH$_2$OCH$_2$.
In certain embodiments, X—Y is CH$_2$CH$_2$O.
In certain embodiments of the invention, $R^3$ is Cl or F.
In certain embodiments of the invention, $R^3$ is Cl.
In certain embodiments of the invention, $R^3$ is F.
In certain embodiments of the invention, $R^2$ is as described above.
In certain embodiments of the invention, $R^2$ is
H,
$C_{1-7}$-alkyl, unsubstituted or substituted with one or more OH, preferably $C_{1-7}$-alkyl,
—CH$_2$-pyridinyl,
—C(O)—$C_{1-7}$-alkyl,
—C(O)CH$_2$NR$^i$R$^{ii}$, wherein R$^i$ and R$^{ii}$ are each independently selected from $C_{1-7}$-alkyl,
—C(O)O—$C_{1-7}$-alkyl, or
—S(O)$_2$NR$^i$R$^{ii}$, wherein R$^i$ and R$^{ii}$ are each independently selected from $C_{1-7}$-alkyl.

Examples for $R^2$ are H, methyl, i-propyl, hydroxyethyl, pyridin-2-yl-methyl, methylcarbonyl, N,N-dimethylamino-methyl-carbonyl, methoxycarbonyl, t-butoxycarbonyl, or N,N-dimethylaminosulfonyl. Preferred $R^2$ is methyl or i-propyl.

In certain embodiments of the invention, $R^2$ is H.
In certain embodiments of the invention, $R^2$ is $C_{1-7}$-alkyl, unsubstituted or substituted with one or more OH, preferably $C_{1-7}$-alkyl.
In certain embodiments of the invention, $R^2$ is methyl.
In certain embodiments of the invention, $R^2$ is i-propyl.
In certain embodiments of the invention, $R^2$ is hydroxyethyl.
In certain embodiments of the invention, $R^2$ is —CH$_2$-pyridinyl.
In certain embodiments of the invention, $R^2$ is pyridin-2-yl-methyl.
In certain embodiments of the invention, $R^2$ is —C(O)—$C_{1-7}$-alkyl.
In certain embodiments of the invention, $R^2$ is methylcarbonyl.

In certain embodiments of the invention, R² is —C(O)CH₂NR'R", wherein R' an R" are each independently selected from C₁₋₇-alkyl.

In certain embodiments of the invention, R² is N,N-dimethylamino-methyl-carbonyl.

In certain embodiments of the invention, R² is —C(O)O—C₁₋₇-alkyl.

In certain embodiments of the invention, R² is methoxycarbonyl.

In certain embodiments of the invention, R² is t-butoxycarbonyl.

In certain embodiments of the invention, R² is S(O)₂NR'R", wherein R' and R" are each independently selected from C₁₋₇-alkyl.

In certain embodiments of the invention, R² is N,N-dimethylaminosulfonyl.

In certain embodiments of the invention, the spirocyclic head groups are selected from
(1s,4's)-3H-spiro[2-benzofuran-1,1'-cyclohexan]-4'-yl,
(1r,4'r)-3H-spiro[2-benzofuran-1,1'-cyclohexan]-4'-yl,
1'H,3H-spiro[2-benzofuran-1,4'-piperidin]-1'-yl,
7-fluoro-1'H,3H-spiro[2-benzofuran-1,4'-piperidin]-1'-yl,
6-fluoro-1'H,3H-spiro[2-benzofuran-1,4'-piperidin]-1'-yl,
5-fluoro-1'H,3H-spiro[2-benzofuran-1,4'-piperidin]-1'-yl,
3-methyl-1'H,3H-spiro[2-benzofuran-1,4'-piperidin]-1'-yl,
3H-spiro[2-benzofuran-1,4'-piperidin]-3-on-1'-yl,
1'H,3H-spiro[2-benzothiophene-1,4'-piperidin]-1'-yl,
2,2-dioxido-1'H,3H-spiro[2-benzothiophene-1,4'-piperidin]-1'-yl,
1H-spiro[isochromene-4,4'-piperidin]-1'-yl,
3,4-dihydro-1'H-spiro[isochromene-1,4'-piperidin]-1'-yl,
(4S)-3'H-spiro[azepane-4,1'-[2]benzofuran]-yl, and
(4R)-3'H-spiro[azepane-4,1'-[2]benzofuran]-yl.

In certain embodiments, the spirocyclic head group HG is

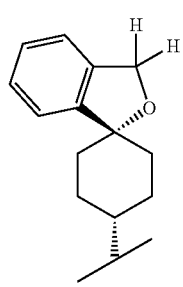

HG-1

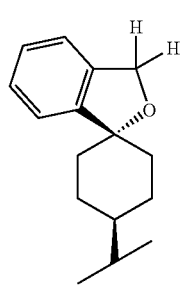

HG-2

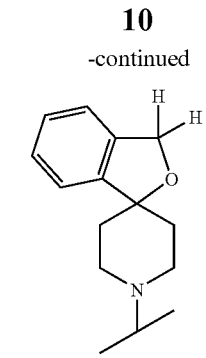

HG-3

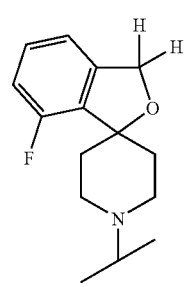

HG-4

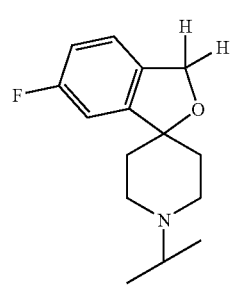

HG-5

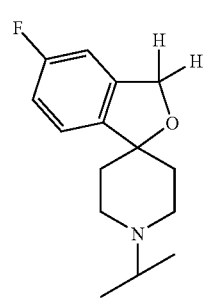

HG-6

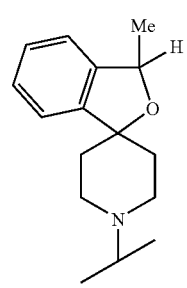

HG-7

In a certain embodiment of the invention, the compound of formula I is provided $$I$$

wherein

X—Y is C(R^aR^b)—O, wherein R^a and R^b are each independently H or methyl,

CH$_2$—S(O)$_p$, wherein p is 0 or 2,

C(O)O,

CH$_2$OCH$_2$,

CH$_2$CH$_2$O, or

Z is CH or N;

R$^1$ is halo, and m is 0 or 1;

R$^2$ is H,

C$_{1-7}$-alkyl, unsubstituted or substituted with one or more OH, preferably C$_{1-7}$-alkyl, —CH$_2$-pyridinyl, —C(O)—C$_{1-7}$-alkyl, —C(O)CH$_2$NR$^i$R$^{ii}$, wherein R$^i$ and R$^{ii}$ are each independently selected from C$_{1-7}$-alkyl, —C(O)O—C$_{1-7}$-alkyl, or —S(O)$_2$NR$^i$R$^{ii}$, wherein R$^i$ and R$^{ii}$ are each independently selected from C$_{1-7}$-alkyl;

R$^3$ is Cl or F, preferably Cl, n is 1 or 2, or a pharmaceutically acceptable salt thereof.

In a certain embodiment of the invention, the compound of formula I is a compound of formula I'

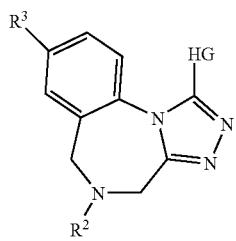

wherein
HG is selected from any one of groups HG-1 to HG-14 as described above,
R² is H,
C₁₋₇alkyl, unsubstituted or substituted with one or more OH, preferably C₁₋₇-alkyl,
—CH₂-pyridinyl,
—C(O)—C₁₋₇-alkyl,
—C(O)CH₂NRⁱRⁱⁱ, wherein Rⁱ and Rⁱⁱ are each independently selected from C₁₋₇-alkyl,
—C(O)O—C₁₋₂-alkyl, or
—S(O)₂NRⁱRⁱⁱ, wherein Rⁱ and Rⁱⁱ are each independently selected from C₁₋₇-alkyl;
R³ is Cl or F, preferably Cl, and
n is 1 or 2,
or a pharmaceutically acceptable salt thereof.

Examples for the compound according to the invention are shown in the experimental part. The table below lists example compounds.

TABLE 2

Structures of selected examples.

| Ex. # | Structure |
|---|---|
| 1 | |
| 2 | |
| 3 | 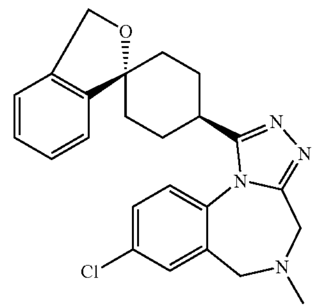 [SMILES: CN1Cc2cc(Cl)ccc2-n2c(nnc2[C@H]2CC[C@@]3(CC2)OCc2ccccc23)C1] |
| 4 | 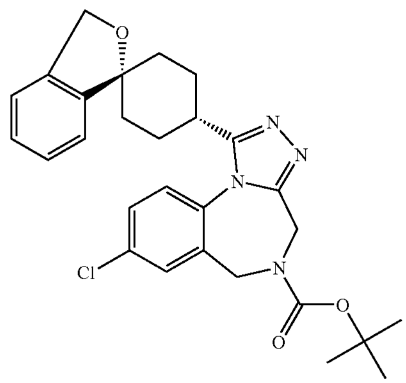 [SMILES: CC(C)(C)OC(=O)N1Cc2cc(Cl)ccc2-n2c(nnc2[C@H]2CC[C@]3(CC2)OCc2ccccc23)C1] |
| 5 | 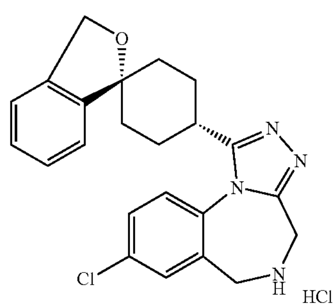 [SMILES: Clc1ccc2c(c1)CNCc1nnc([C@H]3CC[C@]4(CC3)OCc3ccccc34)n1-2 ; Cl] |
| 6 | 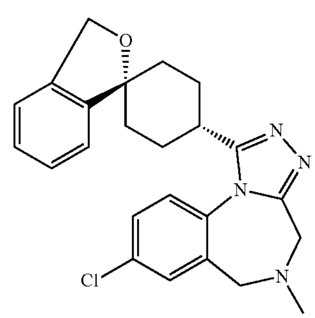 [SMILES: CN1Cc2cc(Cl)ccc2-n2c(nnc2[C@H]2CC[C@]3(CC2)OCc2ccccc23)C1] |

TABLE 2-continued

Structures of selected examples.

| Ex. # | Structure |
|---|---|
| 7 | |
| 8 | |
| 9 | |
| 10 | |
| 11 | 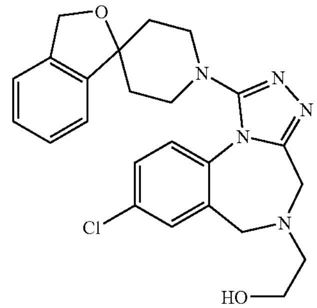 [SMILES: OCCN1Cc2cc(Cl)ccc2-n2c(nnc2N2CCC3(CC2)OCc2ccccc23)C1] |
| 12 | 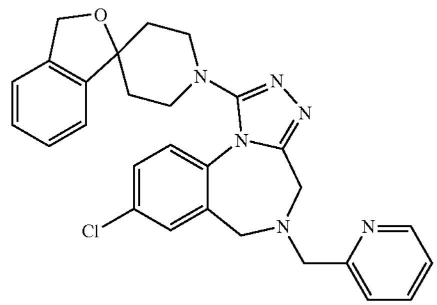 [SMILES: Clc1ccc2c(c1)CN(Cc1ccccn1)Cc1nnc(N3CCC4(CC3)OCc3ccccc34)n1-2] |
| 13 | 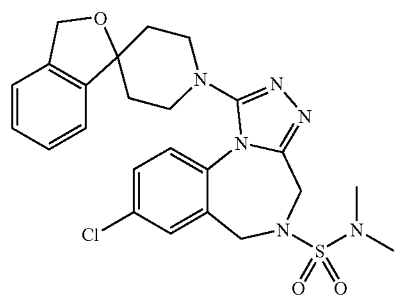 [SMILES: CN(C)S(=O)(=O)N1Cc2cc(Cl)ccc2-n2c(nnc2N2CCC3(CC2)OCc2ccccc23)C1] |
| 14 | 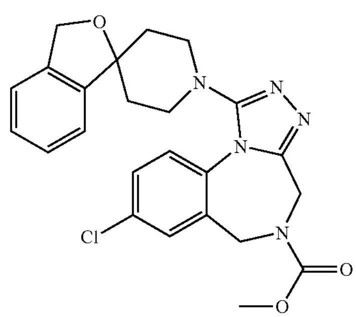 [SMILES: COC(=O)N1Cc2cc(Cl)ccc2-n2c(nnc2N2CCC3(CC2)OCc2ccccc23)C1] |
| 15 | 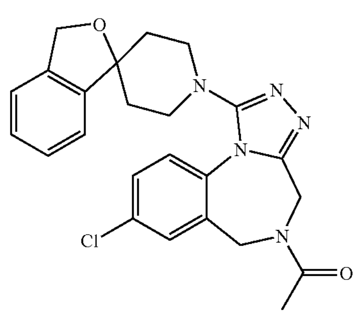 [SMILES: CC(=O)N1Cc2cc(Cl)ccc2-n2c(nnc2N2CCC3(CC2)OCc2ccccc23)C1] |

TABLE 2-continued

Structures of selected examples.

| Ex. # | Structure |
|---|---|
| 16 | (structure) |
| 17 | (structure) |
| 18 | (structure) |
| 19 | (structure) |
| 20 | (structure) |
| 21 | (structure) |
| 22 | (structure) |
| 23 | (structure) |

TABLE 2-continued

Structures of selected examples.

| Ex. # | Structure |
|---|---|
| 24 | 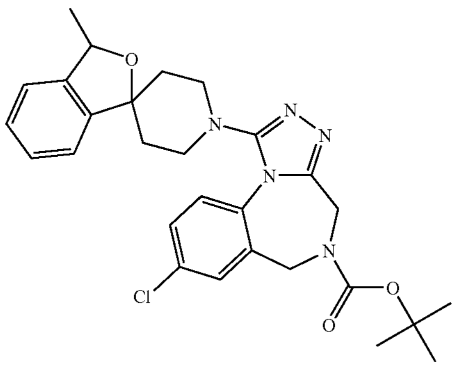 [SMILES: CC1OC2(CCN(c3nnc4n3-c3ccc(Cl)cc3CN(C(=O)OC(C)(C)C)C4)CC2)c2ccccc21] |
| 25 | 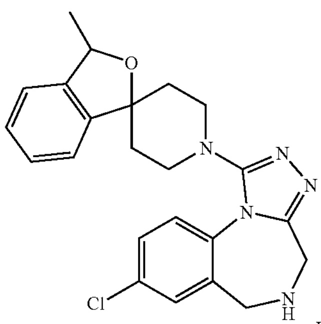 |
| 26 | 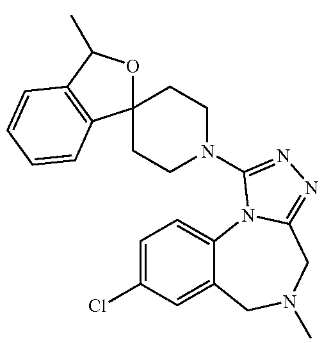 [SMILES: CC1OC2(CCN(c3nnc4n3-c3ccc(Cl)cc3CN(C)C4)CC2)c2ccccc21] |
| 27 | 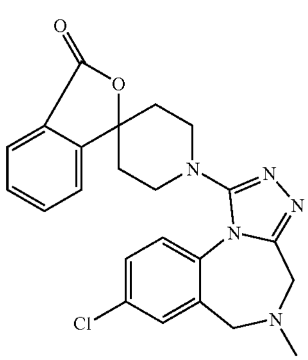 [SMILES: CN1Cc2cc(Cl)ccc2-n2c(nnc2N2CCC3(CC2)OC(=O)c2ccccc23)C1] |
| 28 | 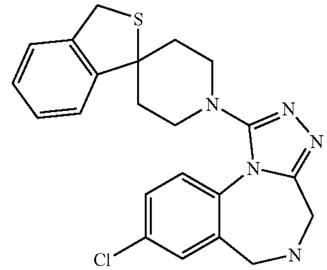 [SMILES: Clc1ccc2c(c1)CNCc1nnc(N3CCC4(CC3)SCc3ccccc34)n1-2] |
| 29 | 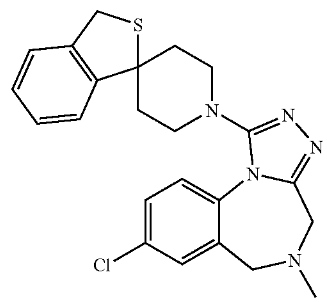 [SMILES: CN1Cc2cc(Cl)ccc2-n2c(nnc2N2CCC3(CC2)SCc2ccccc23)C1] |
| 30 | 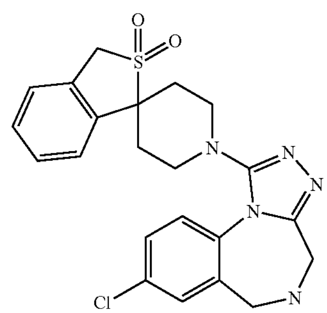 [SMILES: O=S1(=O)Cc2ccccc2C12CCN(c1nnc3n1-c1ccc(Cl)cc1CNC3)CC2] |
| 31 | 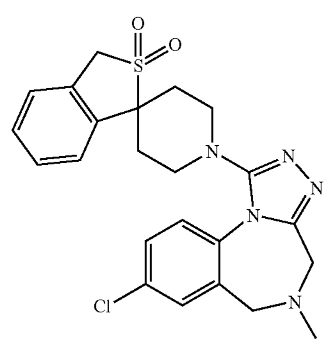 [SMILES: CN1Cc2cc(Cl)ccc2-n2c(nnc2N2CCC3(CC2)c2ccccc2CS3(=O)=O)C1] |
| 32 | 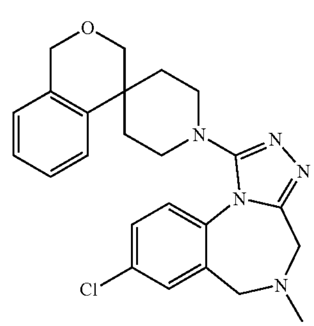 [SMILES: CN1Cc2cc(Cl)ccc2-n2c(nnc2N2CCC3(CC2)COCc2ccccc23)C1] |

TABLE 2-continued

Structures of selected examples.

| Ex. # | Structure |
|---|---|
| 33 | 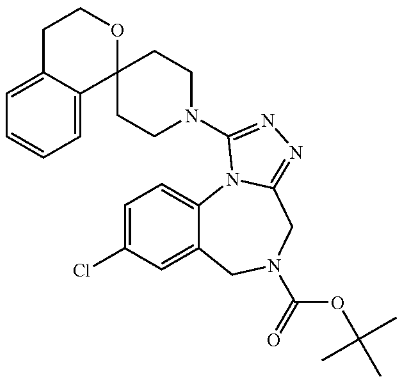 [SMILES: CC(C)(C)OC(=O)N1Cc2cc(Cl)ccc2-n2c(nnc2N2CCC3(CC2)OCCc2ccccc23)C1] |
| 34 | 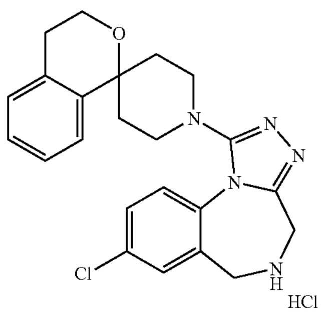 [SMILES: Clc1ccc2c(c1)CNCc1nnc(N3CCC4(CC3)OCCc3ccccc34)n1-2 ; Cl] |
| 35 | 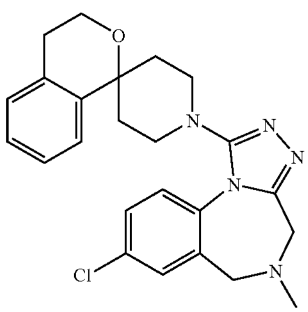 [SMILES: CN1Cc2cc(Cl)ccc2-n2c(nnc2N2CCC3(CC2)OCCc2ccccc23)C1] |
| 36 | 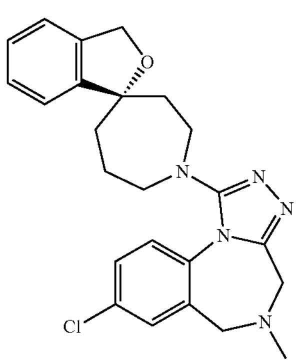 [SMILES: CN1Cc2cc(Cl)ccc2-n2c(nnc2N2CCC[C@@]3(CC2)OCc2ccccc23)C1] |
| 37 | |

Preferred compounds of the invention are shown in the examples. Particularly preferred are:

tert-butyl 8-chloro-1-[(1r,4'r)-3H-spiro[2-benzofuran-1,1'-cyclohexan]-4'-yl]-4H-[1,2,4]triazolo[4,3-a][1,4]benzodiazepine-5(6H)-carboxylate;

8-chloro-1-[(1r,4'r-3H-spiro[2-benzofuran-1,1'-cyclohexan]-4'-yl]-5,6-dihydro-4H-[1,2,4]triazolo[4,3-a][1,4]benzodiazepine hydrochloride;

8-chloro-5-methyl-1-[(1r,4'r)-3H-spiro[2-benzofuran-1,1'-cyclohexan]-4'-yl]-5,6-dihydro-4H-[1,2,4]triazolo[4,3-a][1,4]benzodiazepine;

8-chloro-1-[(1s,4's)-3H-spiro[2-benzofuran-1,1'-cyclohexan]-4'-yl]-5,6-dihydro-4H-[1,2,4]triazolo[4,3-a][1,4]benzodiazepine hydrochloride;

tert-butyl 8-chloro-1-(1H,3H-spiro[2-benzofuran-1,4'-piperidin]-1-yl)-4H-[1,2,4]triazolo[4,3-a][1,4]benzodiazepine-5(6H)-carboxylate;

8-chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine;

8-chloro-5-isopropyl-1-1'H,3H-spiro[2-benzofuran-1,4'-piperidin]-1'-yl)-5,6-dihydro-4H-[1,2,4]triazolo[4,3-a][1,4]benzodiazepine;

8-chloro-5-(pyridin-2-ylmethyl)-1-(1'H,3H-spiro[2-benzofuran-1,4'-piperidin]-1'-yl)-5,6-dihydro-4H[1,2,4]triazolo[4,3-a][1,4]benzodiazepine;

5-acetyl-8-chloro-1-(1'H,3H-spiro[2-benzofuran-1,4'-piperidin]-1'-yl)-5,6-dihydro-4H-[1,2,4]triazolo[4,3-a][1,4]benzodiazepine;

2-[8-chloro-1-(1'H,3H-spiro[2-benzofuran-1,4'-piperidin]-1'-yl)-4H-[1,2,4]triazolo[4,3-a][1,4]benzodiazepin-5(6H)-yl]-N,N-dimethyl-2-oxoethanamine;

tert-butyl 8-chloro-1-(6-fluoro-1'H,3H-spiro[2-benzofuran-1,4'-piperidin]-1'-yl)-4H-[1,2,4]triazolo[4,3-a][1,4]benzodiazepine-5(6H)-carboxylate;

8-chloro-1-(6-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;

8-chloro-1-(7-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;

8-chloro-1-(5-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;

tert-butyl 8-chloro-1-(3-methyl-1'H,3H-spiro[2-benzofuran-1,4'-piperidin]-1'-yl)-4H-[1,2,4]triazolo[4,3-a][1,4]benzodiazepine-5(6H)-carboxylate;

8-chloro-5-methyl-1-(3-methyl-1'H,3H-spiro[2-benzofuran-1,4'-piperidin]-1'-yl)-5,6-dihydro-4H-[1,2,4]triazolo[4,3-a][1,4]benzodiazepine;
1'-(8-chloro-5-methyl-5,6-dihydro-4H-[1,2,4]triazolo[4,3-a][1,4]benzodiazepin-1-yl)-3H-spiro[2-benzofuran-1,4'-piperidin]-3-one;
8-chloro-5-methyl-1-(1'H,3H-spiro[2-benzothiophene-1,4'-piperidin]-1'-yl)-5,6-dihydro-4H-[1,2,4]triazolo[4,3-a][1,4]benzodiazepine;
8-chloro-1-(2,2-dioxido-1H-3H-spiro[2-benzothiophene-1,4'-piperidin]-1'-yl)-5-methyl-5,6-dihydro-4H-[1,2,4]triazolo[4,3-a][1,4]benzodiazepine;
1'-(8-chloro-5-methyl-5,6-dihydro-4H-[1,2,4]triazolo[4,3-a][1,4]benzodiazepin-1-yl)-1H-spiro[isochromene-4,4'-piperidine];
1'-(8-chloro-5-methyl-5,6-dihydro-4H[1,2,4]triazolo[4,3-a][1,4]benzodiazepin-1-yl)-3,4-dihydrospiro[isochromene-1,4'-piperidine];
(+)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran]; and
(−)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran].

Most preferred are the following compounds:
(+)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran],
8-chloro-5-methyl-1-[(1r,4'r)-3H-spiro[2-benzofuran-1,1'-cyclohexan]-4'-yl]-5,6-dihydro-4H-[1,2,4]triazolo[4,3-a][1,4]benzodiazepine,
8-chloro-5-methyl-1-(3-methyl-1'H,3H-spiro[2-benzofuran-1,4'-piperidin]-1'-yl)-5,6-dihydro-4H-[1,2,4]triazolo[4,3-a][1,4]benzodiazepine,
(−)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran],
8-chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine,
1'-(8-chloro-5-methyl-5,6-dihydro-4H-[1,2,4]triazolo[4,3-a][1,4]benzodiazepin-1-yl)-1H-spiro[isochromene-4,4'-piperidine],
8-chloro-1-(6-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine,
8-chloro-5-isopropyl-1-(1'H-3H-spiro[2-benzofuran-1,4'-piperidin]-1'-yl)-5,6-dihydro-4H-[1,2,4]triazolo[4,3-a][1,4]benzodiazepine, and
8-chloro-1-(5-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine.

In a certain embodiment, the compounds of formula (I) of the invention can be manufactured according to a process comprising the step of reacting a compound of formula (II)

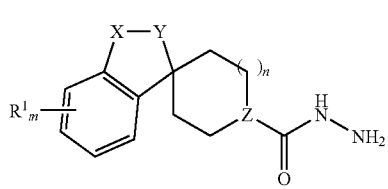

with a compound of formula (III)

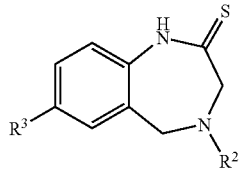

to obtain a compound of formula (I-1) wherein $R^1$, $R^2$, X—Y, m and n are as defined hereinabove for formula (I) and Z equals CH.

In another embodiment, the compounds of formula (I) of the invention can be manufactured according to a process comprising the step of reacting a compound of formula (IV)

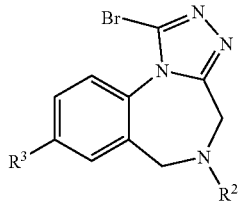

with a compound of formula (IV)

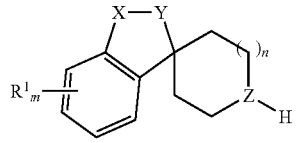

to obtain a compound of formula (I-2) wherein $R^1$, $R^2$, X—Y, m and n are as defined hereinabove for formula (I) and Z equals N.

A certain embodiment of the invention is a compound as described in any of the embodiments obtainable by a process according as described above.

A certain embodiment of the invention is a compound as described in any of the embodiments, whenever obtained by a process according as described above.

A certain embodiment of the invention is a compound as described in any of the embodiments for the use as therapeutically active substance.

A certain embodiment of the invention is a compound as described in any of the embodiments for use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is a pharmaceutical composition comprising a compound as described in any of the embodiments and a pharmaceutically acceptable carrier, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the preparation of a pharmaceutical composition.

A certain embodiment of the invention is a method for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior which comprises administering a compound of the invention.

A certain, embodiment of the invention is a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

These processes are described in more detail with the following general schemes and procedures A to H.

Scheme 1: General Scheme A

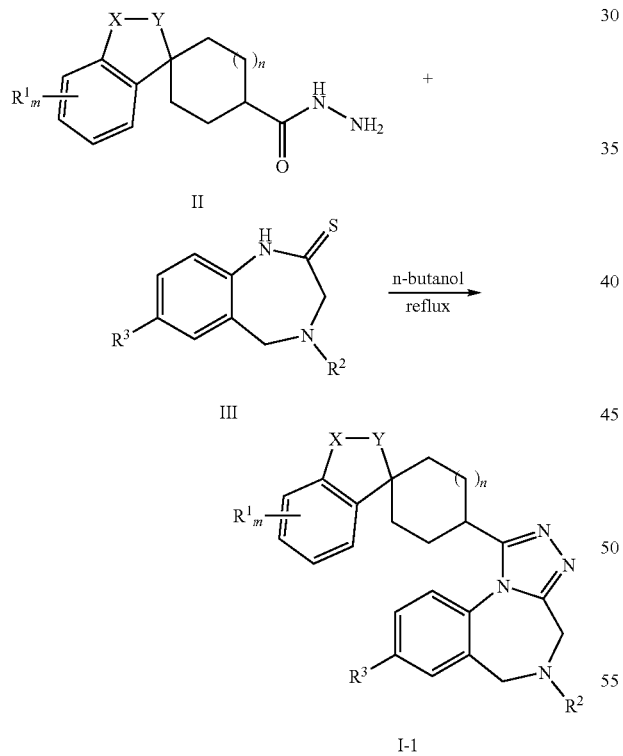

Compounds of formula (I-1) (compounds of formula (I) in which Z is CH) can be prepared by thermal condensation of a hydrazide derivative of formula (II) and a thiolactam derivative of formula (III). Compounds of formula (II) can be prepared following the general scheme E as described hereinafter. The synthesis of compounds of formula (III) is outlined in general scheme D hereinafter. General scheme A is hereinafter further illustrated with general procedure I.

Scheme 2: General Scheme B

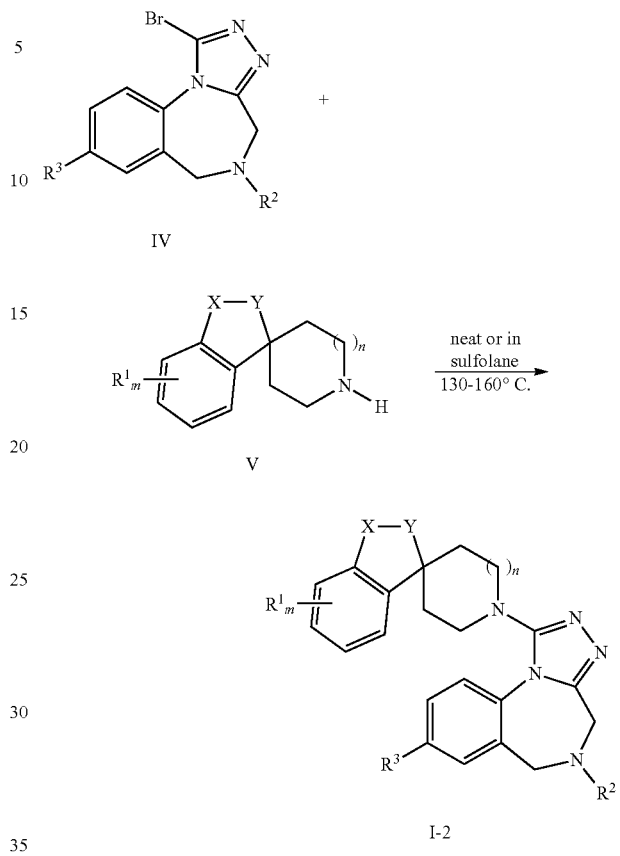

Compounds of formula (I-2) (compounds of formula (I) in which Z is N) can be prepared by thermal condensation of a bromotriazole intermediate of formula (IV) and an amine derivative of formula (V). The synthesis of compounds of formula (IV) is outlined in general scheme D hereinafter. The compounds of formula (V) are either commercially available or prepared using methods known in the art starting from commercially available materials. Alternatively, compounds of formula (V) can be prepared following the general schemes F, G or H as described hereinafter.

Scheme 3: General Scheme C

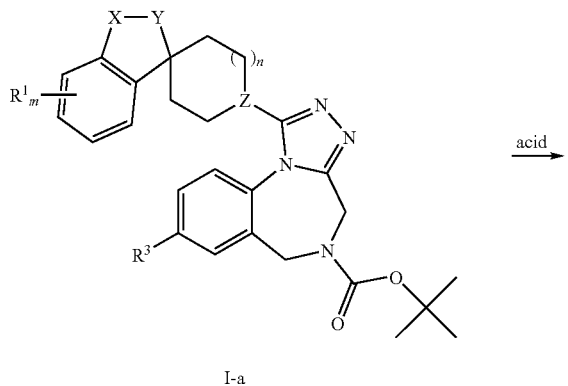

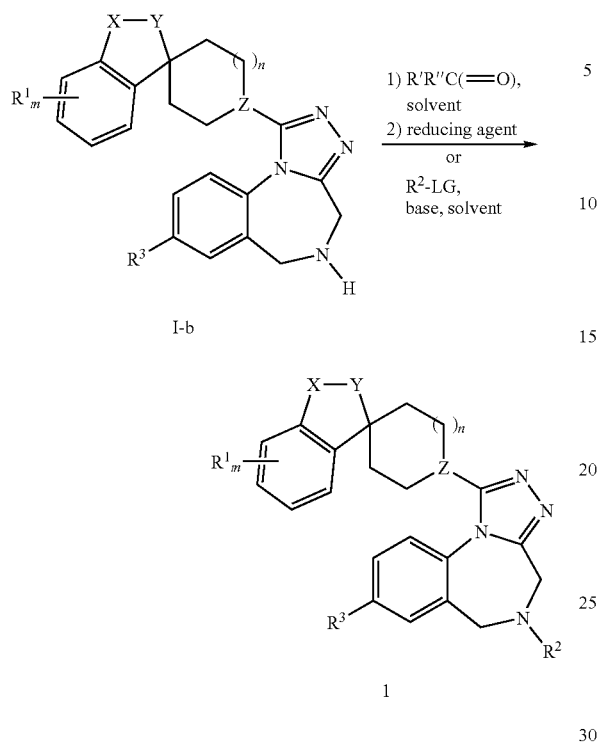

Compounds of formula (I) with R² different from H can be prepared from compounds of formula (I-b) (compounds of formula (I) wherein R² is H) according to methods known in the art, e.g. by treating a compound of formula (I-b) with an inorganic base such as a carbonate salt or an organic base such as a tertiary amine and an electrophilic reactant R²-LG (wherein LG is a leaving group, e.g. halogen or sulfonyl) which is either commercially available or easily prepared according to methods and starting materials well known in the art. Alternatively, compounds of formula (I) can be obtained via reductive alkylation by consecutively treating a compound of formula (I-b) with a ketone or aldehyde and a suitable reducing agent, e.g. a borohydride derivative such as sodium borohydride, sodium cyanoborohydride or sodium triacetoxyborohydride. Compounds of formula (I-b) can be obtained by cleavage of the substituent R² of compound of formula I using methods known in the art. Compounds of formula (I-b) are conveniently obtained as the salt or the free base after basic aqueous work-up by treatment of compounds of formula (I-a) (compounds of formula (I) in which R² is tert-butoxycarbonyl) with an acid in a suitable solvent, e.g. methanesulfonic acid in dichloromethane or tetrahydrofuran or hydrochloric acid in methanol. General scheme C is hereinafter further illustrated with general procedures II and III.

Scheme 4: General Scheme D

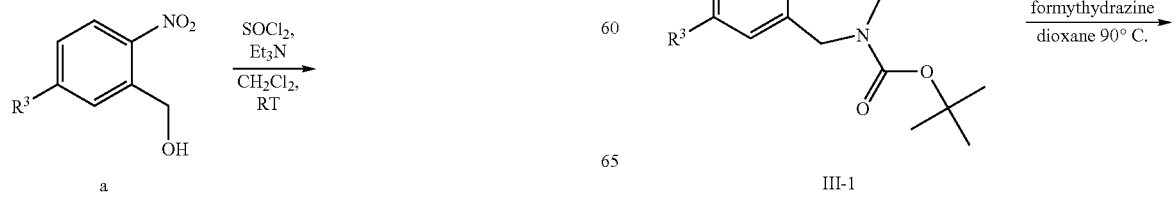

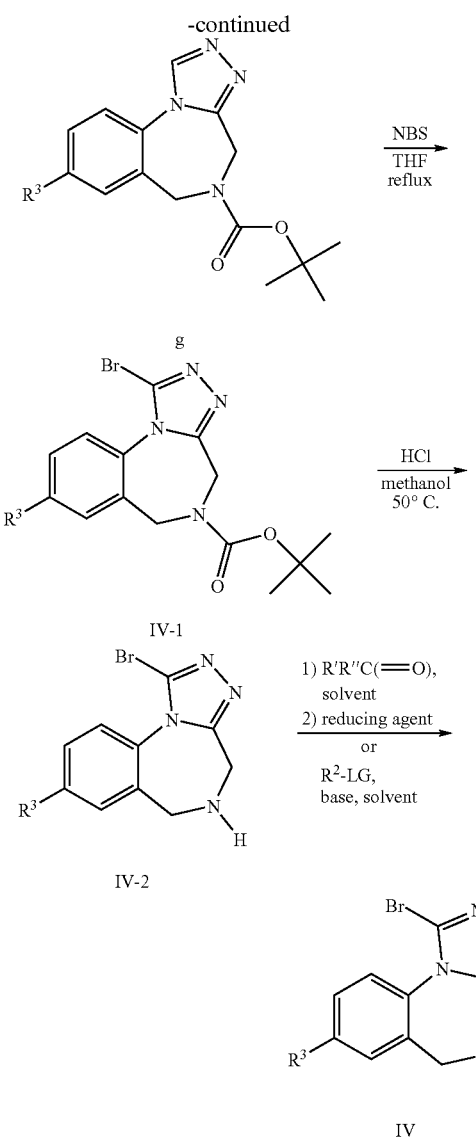

Thiolactam derivatives of formula (III-1) (compounds of formula (III) in which $R^2$ is tert-butoxycarbonyl) and bromotriazole derivatives of formulas (IV), (IV-1) (compounds of formula (IV) in which $R^2$ is tert-butoxycarbonyl), and (IV-2) (compounds of formula (IV) in which $R^2$ is H) can be obtained as follows: Transformation of a 2-nitrobenzyl alcohol of formula (a) to a benzylic chloride of formula (b) can be effected by a chlorinating reagent such as thionyl chloride in the presence of an organic tertiary amine base. Alkylation of a compound of formula (b) with glycine ethyl ester hydrochloride in the presence of an organic tertiary amine base and N-protection of the resulting compound of formula (c) using di-tert-butyl dicarbonate and a catalytic amount of 4-N,N-dimethylaminopyridine gives compounds of formula (d). The nitro group can be reduced selectively by hydrogenation over palladium on charcoal, which has been pretreated with a zinc halide such as zinc bromide, to give aniline intermediates of formula (e). Cyclization to lactams of formula (f) is achieved by treatment of compounds of formula (e) with a suitable base, e.g. potassium tert-butoxide, in tetrahydrofuran. A thiolactam derivative of formula (III-1) is obtained by treatment of a compound of formula (f) with Lawesson's reagent (2,4-bis-(4-methoxyphenyl)-1,3,2,4-dithiadiphosphetane-2,4-disulfide) or phosphorous penta-sulfide at elevated temperature. A thiolactam of formula (III-1) can be converted to a triazole derivative of formula (g) by condensation with formylhydrazine. A compound of formula (IV-1) (compounds of formula (IV) wherein $R^2$ is tert-butoxycarbonyl) can be obtained by reacting a compound of formula (g) with a suitable brominating agent such as N-bromosuccinimide. Compounds of formula (IV-2) (compounds of formula (IV) wherein $R^2$ is H) are obtained as the salt or the free base after basic aqueous work-up by treatment of compounds of formula (IV-1) with an acid in a suitable solvent, e.g. methanesulfonic acid in dichloromethane or tetrahydrofuran or hydrochloric acid in methanol. Compounds of formula (IV) with $R^2$ different from H can be prepared using methods known in the art, e.g. by treating a compound of formula (IV-2) with an inorganic base such as a carbonate salt or an organic base such as a tertiary amine and an electrophilic reactant $R^2$-LG (wherein LG is a leaving group, e.g. halogen or sulfonyl) which is either commercially available or easily prepared according to methods and starting materials well known in the art. Alternatively, compounds of formula (IV) can be obtained via reductive alkylation by consecutively treating a compound of formula (I-b) with a ketone or aldehyde and a suitable reducing agent, e.g. a borohydride derivative such as sodium borohydride, sodium cyanoborohydride or sodium triacetoxyborohydride. Compounds of formula (IV-3) (compounds of formula (IV) wherein $R^2$ is methyl) can be prepared by reductive methylation using paraformaldehyde.

Scheme 5: General Scheme E

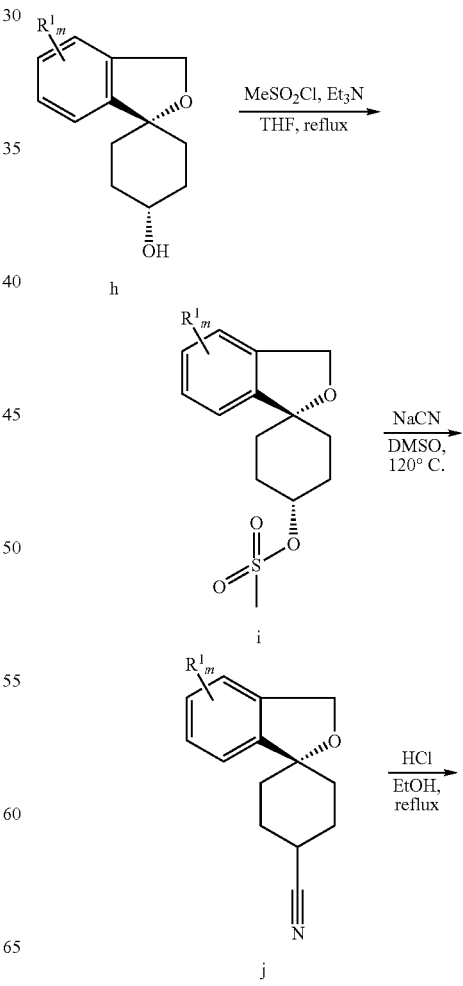

Scheme 6: General Scheme F

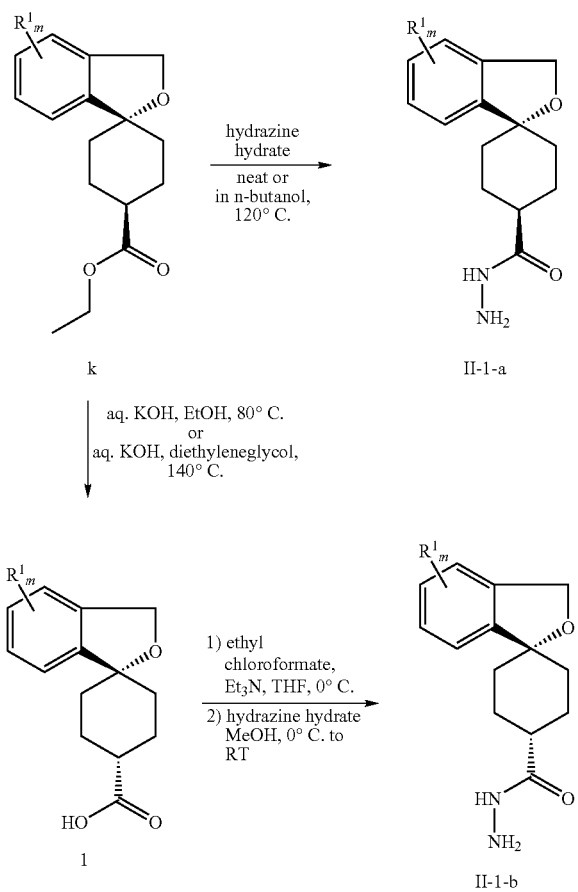

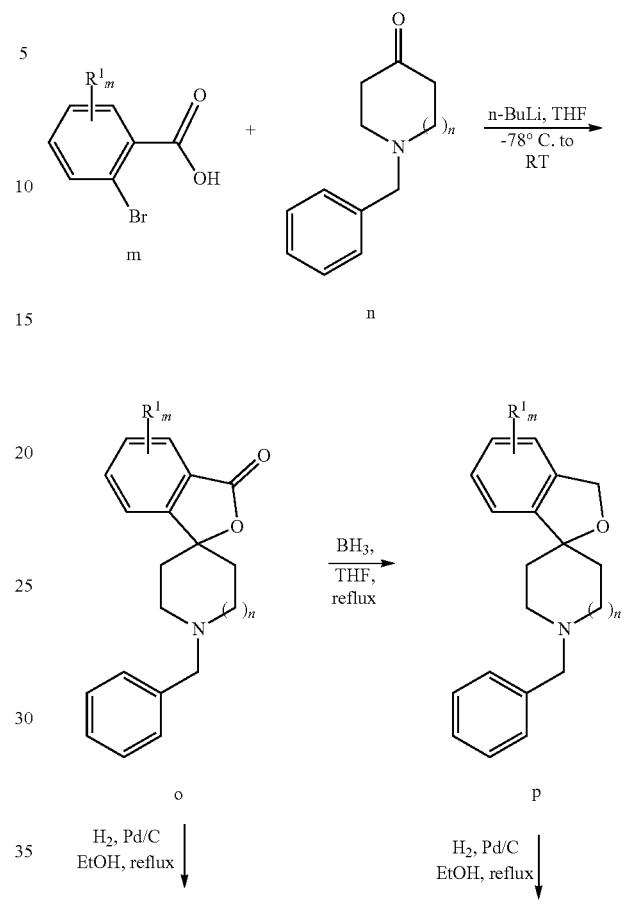

Hydrazide intermediates of formula (II-1) (compounds of formula (II) in which X—Y is CH$_2$—O and n equals 1) can be prepared as described hereinafter starting from secondary alcohol intermediates of formula (h). The latter can be prepared according to a method described in the literature (F. J. Urban, G. Anderson; Organic Process Research & Development 1999, 3, 460-464). A methanesulfonic acid ester of formula (i) can be obtained by treatment of a compound of formula (h) with methanesulfonyl chloride and a tertiary amine base. Treatment of a compound of formula (i) with sodium cyanide in dimethylsulfoxide yields a nitrite derivative of formula (j), which can be solvolyzed to an ester intermediate of formula (k) in refluxing ethanolic hydrogen chloride solution. A compound of formula (k) can be converted to a hydrazide derivative of formula (II-1-a) (a compound of formula (II-1) in which the hydrazide and phenyl groups are oriented cis relative to each other) by heating with hydrazine hydrate. Alternatively, an ester derivative of formula (k) can be hydrolyzed under epimerization to a carboxylic acid derivative of formula (I) using potassium hydroxide in ethanol at 80° C. or in diethyleneglycol at 140° C. A hydrazide derivative of formula (II-1-b) (a compound of formula (II-1) in which the hydrazide and phenyl groups are oriented trans relative to each other) can be obtained by activating an acid intermediate of formula (I), e.g. with ethyl chloroformate, thionyl chloride, oxalylchloride or a peptide coupling reagent, and subsequent coupling with hydrazine.

Amine intermediates of formulas (V-1) (compounds of formula (V) in which X—Y is C(=O)—O) and (V-2) (compounds of formula (V) in which X—Y is CH$_2$—O) can be prepared as described hereinafter: Double-lithiation of a 2-bromobenzoic acid derivative of formula (m) via deprotonation and bromine-lithium exchange with an alkyllithium reagent and subsequent addition to a cyclic ketone derivative of formula (n) leads to a spirolactone derivative of formula (o). Reduction of the carbonyl group of a lactone of formula (o) gives a compound of formula (p). Amine derivatives of formulas (V-1) and (V-2) are obtained by palladium-catalyzed hydrogenolytic N-debenzylation of compounds of formulas (o) and (p), respectively.

Scheme 7: General Scheme G

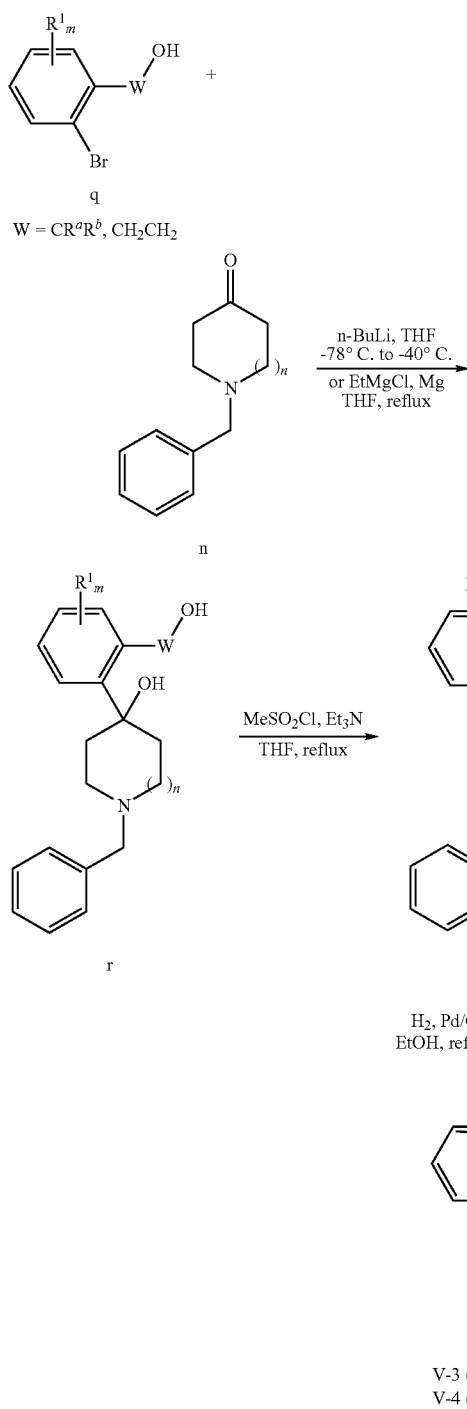

Amine intermediates of formulas (V-3) (compounds of formula (V) in which X—Y is $CR^aR^b$—O) and (V-4) (compounds of formula (V) in which X—Y is $CH_2$—$CH_2$—O) can be prepared as described hereinafter: Double-metallation of an 2-bromoaryl substituted aliphatic alcohol derivative of formula (q) via O-deprotonation and bromine-metal exchange with magnesium or a Grignard or alkyllithium reagent and subsequent addition to a cyclic ketone derivative of formula (n) leads to a Spiro derivative of formula (s).

Amine derivatives of formulas (V-3) and (V-4) are obtained by palladium-catalyzed hydrogenolytic N-debenzylation of a compound of formula(s).

Scheme 8: General Scheme H

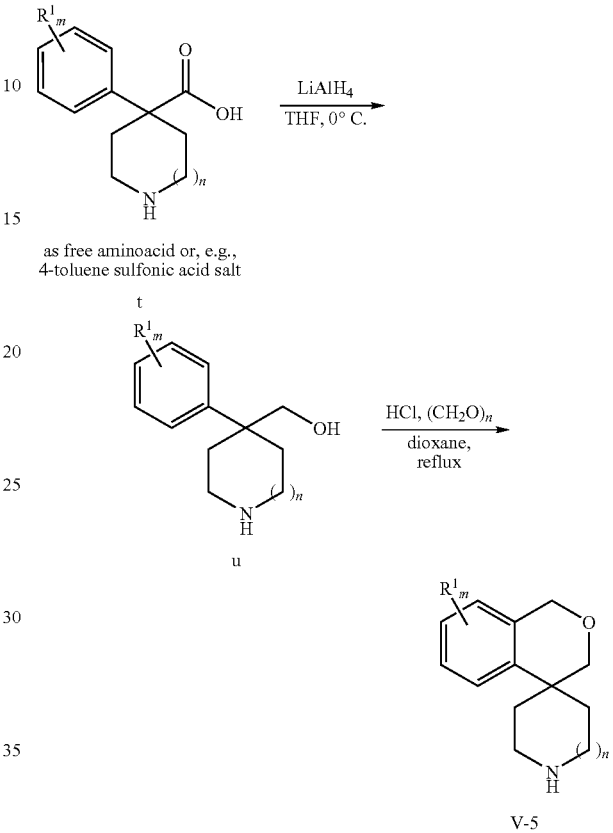

Amine intermediates of formula (V-5) (compounds of formula (V) in which X—Y is $CH_2$—O—$CH_2$) can be prepared as described hereinafter: Reduction of a piperidine or azepane derivative of formula (t), which is substituted geminally in the 4-position with an aryl group and a carboxylic acid group, can be reduced to an aminoalcohol derivative of formula (u) with a reducing agent such as lithium aluminum hydride. Cyclization of a derivative of formula (u) with formaldehyde in the presence of hydrochloric acid gives a spiro-derivative of formula (V-5).

The compounds of the present invention exhibit V1a activity. They are selective inhibitors of the V1a receptor and are therefore likely to have a low potential to cause unwanted off-target related side-effects. The V1a activity can be detected as described below.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 μl of bead/membrane mixture is then added to each well of a 96 well plate, followed by 50 μl of 4 nM 3H-Vasopressin (American Radiolabeled Chemicals). For total binding measurement 100 μl of binding buffer are added to the respective wells, for non-specific binding 100 μl of 8.4 mM cold vasopressin and for compound testing 100 μl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V1a receptor of compounds according to present invention.

TABLE 3

Human V1a receptor of selected examples

| Ex.# | pKi hV1a |
|---|---|
| 1 | 8.34 |
| 2 | 7.40 |
| 3 | 8.55 |
| 5 | 7.79 |
| 7 | 8.35 |
| 9 | 8.62 |
| 10 | 8.74 |
| 12 | 8.74 |
| 15 | 8.38 |
| 16 | 8.17 |
| 17 | 7.99 |
| 19 | 8.12 |
| 22 | 8.40 |
| 23 | 8.68 |
| 24 | 7.97 |
| 26 | 8.32 |
| 27 | 7.91 |
| 29 | 8.76 |
| 31 | 7.32 |
| 32 | 8.66 |
| 35 | 7.98 |
| 36 | 8.84 |
| 37 | 8.30 |

Pharmaceutical Compositions

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it, but merely as being representative thereof. All temperatures are given in degrees Celsius.

Examples of compositions according to the invention are:

Example A

Tablets of the following composition are manufactured in the usual manner:

TABLE 4 possible tablet composition

| ingredient | mg/tablet | | | |
|---|---|---|---|---|
|  | 5 | 25 | 100 | 500 |
| 1. Compound of formula I | 5 | 25 | 100 | 500 |
| 2. Lactose | 45 | 105 | 30 | 150 |
| 3. Corn Starch | 15 | 6 | 6 | 60 |
| 4. Microcrystalline Cellulose | 34 | 30 | 30 | 450 |
| 5. Magnesium Stearate | 1 | 1 | 1 | 1 |
| Total | 100 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 5 possible capsule ingredient composition

| ingredient | mg/capsule | | | | |
|---|---|---|---|---|---|
|  | 5 | 10 | 25 | 100 | 500 |
| 1. Compound of formula I | 5 | 10 | 25 | 100 | 500 |
| 2. Lactose | 159 | 155 | 123 | 148 | — |
| 3. Corn Starch | 25 | 30 | 35 | 40 | 70 |
| 4. Talc | 10 | 5 | 15 | 10 | 25 |
| 5. Magnesium Stearate | 1 | — | 2 | 2 | 5 |
| Total | 200 | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatine capsules.

Example B-2

Soft Gelatine Capsules of the following composition are manufactured:

TABLE 6 possible soft gelatine capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 7 possible soft gelatine capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 8 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, and the suppositories are then removed from the moulds and packed individually in wax paper or metal foil.

Example D

Injection solutions of the following composition are manufactured:

TABLE 9 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 10 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples 1-37 are provided for illustration of the invention. They should not be considered as limiting the scope of the invention, but merely as being representative thereof.

Hydrazide Intermediates of Formula (II)

Hydrazide 1

(1r,4'r)-3H-Spiro[2-benzofuran-1,1'-cyclohexane]-4'-carbohydrazide a) (1s,4's)-3H-Spiro[2-benzofuran-1,1'-cyclohexan]-4'-ol To a solution of 3H,4'H-spiro[2-benzofuran-1,1'-cyclohexan]-4'-one (2.5 g, 12 mmol) in ethanol (36 ml) was added sodium borohydride (0.69 g, 18 mmol) at room temperature with cooling on a water bath. After stirring for 16 h, 2 M aqueous hydrogen chloride solution was added to the reaction mixture. The solvent was evaporated and the aqueous residue was extracted with two portions of ethyl acetate. The combined organic layers were washed with brine, dried over anhydrous sodium sulfate and concentrated in vacuo. Flash chromatography with n-heptane/ethyl acetate as eluent gave the title compound (1.95 g, 78.9%) as light yellow solid. MS m/e: 204 (M+).

b) (1s,4's)-3H-Spiro[2-benzofuran-1,1'-cyclohexan]-4'-yl methanesulfonate

To a solution of (1s,4's)-3H-spiro[2-benzofuran-1,1'-cyclohexan]-4'-ol (0.70 g, 3.4 mmol) and triethylamine (0.48 ml, 3.4 mmol) in dichloromethane (17 ml) was added methanesulfonyl chloride (0.27 ml, 3.4 mmol) at 0-5° C. Stirring for 1 h was followed by washing with water and brine. The organic layer was dried over anhydrous sodium sulfate and concentrated in vacuo to give the title compound (0.91 g, 94%) as off-white solid. MS m/e: 341 (M+AcO−).

c) (1r,4'r)-3H-Spiro[2-benzofuran-1,1'-cyclohexane]-4'-carbonitrile

A solution of (1s,4's)-3H-spiro[2-benzofuran-1,1'-cyclohexan]-4'-yl methanesulfonate (0.91 g, 3.2 mmol) and sodium cyanide (0.31 g, 6.4 mmol) in dimethylsulfoxide (6.4 ml) was stirred for 30 min at 120° C. The reaction mixture was allowed to cool to room temperature and diluted with 1 M aqueous sodium carbonate solution. After extraction with three portions of tert-butyl methyl ether the combined organic layers were washed with two portions of water and with brine, dried over anhydrous sodium sulfate and concentrated in vacuo. Flash chromatography with n-heptane/ethyl acetate as eluent gave the title compound (0.41 g, 60%) as colorless oil. MS m/e: 213 (M+)

d) Ethyl (1r,4'r)-3H-spiro[2-benzofuran-1,1'-cyclohexane]-4'-carboxylate

A mixture of (1r,4'r)-3H-spiro[2-benzofuran-1,1'-cyclohexane]-4'-carbonitrile (0.40 g, 1.9 mmol) and concentrated hydrochloric acid solution (4.7 ml, 56 mmol) in ethanol (20 ml) was heated at reflux for 72 h. After cooling to room temperature the reaction mixture was poured on ice and basified with 32% aqueous sodium hydroxide solution. The mixture was extracted with two portions of tert-butyl methyl ether. The combined organic layers were washed with 1 M aqueous sodium hydroxide solution, dried over anhydrous sodium sulfate and concentrated in vacuo. Flash chromatography with n-heptane/ethyl acetate as eluent gave the title compound (0.20 g, 41%) as white solid. MS m/e: 260 (M+).

e) (1r,4'r)-3H-Spiro[2-benzofuran-1,1'-cyclohexane]-4'-carbohydrazide

A mixture of ethyl (1r,4'r)-3H-spiro[2-benzofuran-1,1'-cyclohexane]-4'-carboxylate (0.2 g, 0.8 mmol) and hydrazine hydrate (0.04 ml, 0.7 mmol) was heated at reflux for 4 h. Another portion of hydrazine hydrate (0.04 ml, 0.7 mmol) was added, and the reaction mixture was heated at reflux for further 18 h. After cooling to room temperature n-butanol (0.5 ml) and another portion of hydrazine hydrate (0.07 ml, 1.4 mmol) were added and the reaction mixture was heated at reflux for 4 more hours. The mixture was allowed to cool to room temperature, diluted with ethyl acetate (30 ml) and washed with 1 M aqueous sodium hydroxide solution (30 ml). The organic layer was dried over anhydrous sodium sulfate and concentrated in vacuo to give the title compound (0.16 g, 87%) as white solid. MS m/e: 247 (M+H+).

Hydrazide 2

(1s,4's)-3H-Spiro[2-benzofuran-1,1'-cyclohexane]-4'-carbohydrazide a) (1 s,4's)-3H-Spiro[2-benzofuran-1,1'-cyclohexane]-4'-carboxylic acid Preparation of batch 1 of the crude title compound: A mixture of (1r,4'r)-3H-spiro[2-benzofuran-1,1'-cyclohexane]-4'-carbonitrile (0.15 g, 0.70 mmol) in ethanol (7 ml) and 2 M aqueous potassium hydroxide solution (0.88 ml) was heated at reflux for 16 h. The reaction mixture was diluted with diethyleneglycol (10 ml) and stirred for 4 h at 130° C. After cooling to room temperature the reaction mixture was diluted with tert-butyl methyl ether and extracted with two portions of 0.5 M aqueous sodium hydroxide solution. The combined aqueous layers were washed with tert-butyl methyl ether and then acidified with concentrated hydrochloric acid solution. The acidic aqueous layer was extracted with two portions of tert-butyl methyl ether. The combined organic layers were dried over anhydrous sodium sulfate and concentrated in vacuo to give the crude title compound (0.05 g) as light brown solid.

Preparation of batch 2 of the crude title compound: A mixture of (1r,4'r)-3H-spiro[2-benzofuran-1,1'-cyclohexane]-4'-carbonitrile (0.48 g, 2.3 mmol) in diethyleneglycol (15 ml) and 3 M aqueous potassium hydroxide solution (7.5 ml) was stirred at 140° C. for 72 h. After cooling to room temperature the reaction mixture was diluted with tert-butyl methyl ether and extracted with two portions of 0.5 M aqueous sodium hydroxide solution. The combined aqueous layers were washed with tert-butyl methyl ether and then acidified with concentrated hydrochloric acid solution. The acidic aqueous layer was extracted with two portions of tert-butyl methyl ether. The combined organic layers were dried over anhydrous sodium sulfate and concentrated in vacuo to give the crude title compound (0.4 g).

The two batches of the crude title compound were combined and purified by flash chromatography to give the pure title compound (0.30 g, 57%) as white solid. MS m/e: 231 (M−H$^+$).

b) (1s,4's)-3H-Spiro[2-benzofuran-1,1'-cyclohexane]-4'-carbohydrazide

To a solution of (1s,4's)-3H-spiro[2-benzofuran-1,1'-cyclohexane]-4'-carboxylic acid (0.16 g, 0.67 mmol) and triethylamine (0.098 ml, 0.70 mmol) in tetrahydrofuran (7 ml) was added ethyl chloroformate (0.067 ml, 0.70 mmol) at 0° C. The reaction mixture was stirred for 30 min. The ammonium salts were filtered off and the filtrate was added to a solution of hydrazine hydrate (0.065 g, 1.3 mmol) in methanol (7 ml). The reaction mixture was stirred for 18 h at RT. Addition of ethyl acetate (100 ml) was followed by washing with 1 M aqueous sodium hydroxide solution (100 ml) and brine (100 ml). The combined aqueous layers were extracted with ethyl acetate (100 ml). The combined organic layers were dried over anhydrous sodium sulfate and concentrated in vacuo to give the title compound (0.16 g, 96%) as white solid. MS m/e: 247 (M+H$^+$).

Intermediate of formula (III-1)

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 min while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M$^+$).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H$^+$).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H$^+$).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol).

The reaction mixture was purged with argon after 15 min. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 min the precipitate was collected by filtration. The organic layer was separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M−H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tort-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M–H$^+$).

Intermediates of Formula (IV)

Bromotriazole 1

1-Bromo-8-chloro-4H,6H-2,3,5,10b-tetraaza-benzo[e]azulene-5-carboxylic acid tert-butyl ester a) 8-Chloro-4H,6H-2,3,5,10b-tetraaza-benzo[e]azulene-5-carboxylic acid tert-butyl ester Formylhydrazine (10.7 g, 160 mmol) was added over a period of 4 hours to a solution of 7-chloro-2-thioxo-1,2,3,5-tetrahydro-benzo[e][1,4]diazepine-4-carboxylic acid tert-butyl ester (10.0 g, 32.0 mmol) in dioxane (200 ml) at 90° C. The reaction mixture was stirred at 90° C. overnight, then evaporated. The residue was purified by chromatography (300 g silica gel, heptane: ethyl acetate, 8:2 to 0:1) to yield 7.71 g (75%) 8-chloro-4H,6H-2,3,5,10b-tetraaza-benzo[e]azulene-5-carboxylic acid tert-butyl ester as white solid. MS m/e: 379 ([M+CH$_3$COO$^-$])

b) 1-Bromo-8-chloro-4H,6H-2,3,5,10b-tetraaza-benzo[e]azulene-5-carboxylic acid tert-butyl ester N-Bromosuccinimide (4.50 g, 24.0 mmol) was added to 8-chloro-4H,6H-2,3,5,10b-tetraaza-benzo[e]azulene-5-carboxylic acid tert-butyl ester (7.00 g, 21.8 mmol) in tetrahydrofuran (140 ml). The mixture was stirred in boiling tetrahydrofuran for 2 hours. The solvent was removed in vacuo and the residue was purified by chromatography (50 g silica gel, heptane: ethylacetate 1:9 to 1:0) to yield 7.39 g (85%) 1-bromo-8-chloro-4H,6H-2,3,5,10b-tetraaza-benzo[e]azulene-5-carboxylic acid tert-butyl ester as white solid. MS m/e: 401 (M+H$^+$).

Bromotriazole 2

1-Bromo-8-chloro-5,6-dihydro-4H-2,3,5,10b-tetraaza-benzo[e]azulene

A solution of 1-bromo-8-chloro-4H,6H-2,3,5,10b-tetraaza-benzoazulene-5-carboxylic acid tert-butyl ester (3.0 g, 7.6 mmol) in 1.25 M methanolic hydrogen chloride solution (60 ml, 76 mmol) was heated at 50° C. for 10 min. The reaction mixture was poured on 1 M aqueous sodium hydroxide solution (200 ml) and extracted with ethyl acetate. The organic layer was washed with brine, dried over anhydrous sodium sulfate and concentrated in vacuo to give the title compound (1.9 g, 84%) as light yellow solid. MS m/e: 255 (M+H$^+$).

Bromotriazole 3

1-Bromo-8-chloro-5-methyl-5,6-dihydro-4H-2,3,5,10b-tetraaza-benzoazulene

A mixture of 1-bromo-8-chloro-5,6-dihydro-4H-2,3,5,10b-tetraaza-benzo[e]azulene (1.9 g, 6.4 mmol) and paraformaldehyde (1.5 g, 51 mmol) in methanol (64 ml) was heated at reflux for 16 h. After cooling to 0° C. sodium cyanoborohydride (0.8 g, 13 mmol) was added. The reaction mixture was allowed to warm to room temperature and stirred for 3 h. After quenching with 1 M aqueous sodium hydroxide solution (200 ml) the aqueous layer was extracted with ethyl acetate. The organic layer was dried over anhydrous sodium sulfate and concentrated in vacuo. Flash chromatography over aminopropyl-modified silica gel with n-heptane/ethyl acetate as eluent gave the title compound (0.61 g) as white solid with a purity of ca. 85% as assessed by $^1$H-NMR. MS m/e: 313 (M+H$^+$).

Amine Intermediates of Formula (V)

Amine 1

5-Fluoro-3H-spiro[2-benzofuran-1,4'-piperidine]

a) 1'-Benzyl-5-fluoro-3H-spiro[2-benzofuran-1,4'-piperidin]-3-one

To a stirred solution of 2-bromo-5-fluorobenzoic acid (5.0 g, 21.9 mmol) at −70° C. in tetrahydrofuran (30 ml) was added dropwise a 1.6M n-butyllithium solution in hexane (44 ml, 70.1 mmol) over a period of 1 hour. After 3 hours, a solution of 1-benzyl-4-piperidone (8.5 g, 43.8 mmol) in tetrahydrofuran (20 ml) was added dropwise. The mixture was allowed to warm to room temperature and stirred overnight. The mixture was poured into a stirred mixture of water (150 ml) and ether (150 ml). The aqueous layer was extracted with ether (2×40 ml), acidified with HCl 5 N (20 ml) to pH 2 and boiled for 1 hour. The mixture was cooled to 0° C., basified (pH 10) with NaOH 5 N and rapidly extracted with dichloromethane (3×80 ml). The combined extracts were washed with water (80 ml), dried over Na$_2$SO$_4$, filtered and concentrated in vacuo. The crude oil was chromatographed on silica gel (eluent: heptane/ethylacetate 1:1) to yield 2.27 g (33%) of 1'-benzyl-5-fluoro-3H-spiro[2-benzofuran-1,4'-piperidin]-3-one as light yellow solid. MS m/e: 312 (M+H$^+$).

b) 5-Fluoro-3H-spiro[2-benzofuran-1,4'-piperidin]-3-one

1'-Benzyl-5-fluoro-3H-spiro[2-benzofuran-1,4'-piperidin]-3-one (0.622 g, 2 mmol) was suspended in ethanol (6 ml). The mixture was acidified with a few drops of HCl 37%. Pd/C 10% (65 mg, 0.06 mmol) was added. The mixture was refluxed under an hydrogen atmosphere for 1 hour then cooled to room temperature, purged with argon and diluted with dichloromethane. The catalyst was filtered and the filtrate was concentrated in vacuo. The white solid was dissolved in water (20 ml). The solution was basified with a 2M Na$_2$CO$_3$ solution and extracted 3 times with dichloromethane. The combined extracts were dried over Na$_2$SO$_4$, filtered and concentrated in vacuo to yield 0.42 g (96%) 5-fluoro-3H-spiro[2-benzofuran-1,4'-piperidin]-3-one as a white solid. MS m/e: 222 (M+H$^+$).

c) 5-Fluoro-3H-spiro[2-benzofuran-1,4'-piperidine]

To a suspension of 5-fluoro-3H-spiro[2-benzofuran-1,4'-piperidin]-3-one (420 mg, 1.9 mmol) in tetrahydrofuran (4.2 ml) was added dropwise a 1M borane solution in tetrahydrofuran (3.8 ml, 3.8 mmol) at 0° C. The mixture was refluxed overnight and then cooled to 0° C. HCl 5 N (2 ml) was added dropwise. The mixture was refluxed for 5 hours, cooled to 0° C., diluted with water and basified with NaOH 5 N (pH 10). The mixture was extracted 3 times with ethyl acetate. The combined extracts were dried over $Na_2SO_4$, filtered and concentrated in vacuo. The residue was stirred with ether and filtrated. The filtrate was concentrated in vacuo to provide 0.22 g (55%) of 5-fluoro-3H-spiro[2-benzofuran-1,4'-piperidine] as a light yellow oil.

MS m/e: 208 (M+H$^+$).

Amine 2

6-Fluoro-3H-spiro[2-benzofuran-1,4'-piperidine]

a) 1'-Benzyl-6-fluoro-3H-spiro[2-benzofuran-1,4'-piperidin]-3-one

Following the procedure described for the synthesis of 1-benzyl-5-fluoro-3H-spiro[2-benzofuran-1,4'-piperidin]-3-one using 2-bromo-4-fluorobenzoic acid instead of 2-bromo-5-fluorobenzoic acid, the title compound was obtained as an off-white solid (41% yield).

MS m/e: 312 (M+H$^+$).

b) 1'-Benzyl-6-fluoro-3H-spiro[2-benzofuran-1,4'-piperidine]

To a suspension of 1-benzyl-6-fluoro-3H-spiro[2-benzofuran-1,4'-piperidin]-3-one (3 g, 9.6 mmol) in tetrahydrofuran (40 ml) was added dropwise a 1M borane solution in tetrahydrofuran (20 ml, 20 mmol) at 0° C. The mixture was refluxed overnight and then cooled to 0° C. HCl 5N (2 ml) was added dropwise. The mixture was refluxed for 5 hours, cooled to 0° C., diluted with water and basified with NaOH 5 N (pH 10). The mixture was extracted 3 times with ethyl acetate. The combined extracts were dried over $Na_2SO_4$, filtered and concentrated in vacuo. The residue was chromatographed on silica gel (eluent: heptane: ethylacetate 8:2) to yield 2 g (71%) of 1'-benzyl-6-fluoro-3H-spiro[2-benzofuran-1,4'-piperidine] as a colorless oil. MS m/e: 298 (M+H$^+$).

c) 6-Fluoro-3H-spiro[2-benzofuran-1,4'-piperidine]

To a solution of 1'-benzyl-6-fluoro-3H-spiro[2-benzofuran-1,4'-piperidine] (1 g, 3.4 mmol) in ethanol (10 ml) was added Pd/C 10% (100 mg, 0.09 mmol). The mixture was refluxed under an hydrogen atmosphere for 8 hours then cooled to room temperature and purged with argon. The catalyst was filtered and the filtrate was concentrated in vacuo to yield 0.67 g (96%) 6-fluoro-3H-spiro[2-benzofuran-1,4'-piperidine] as a white solid. MS m/e: 208 (M+H$^+$).

Amine 3

7-Fluoro-3H-spiro[2-benzofuran-1,4'-piperidine]

a) 1'-Benzyl-7-fluoro-3H-spiro[2-benzofuran-1,4'-piperidin]-3-one

Following the procedure described for the synthesis of 1-benzyl-5-fluoro-3H-spiro[2-benzofuran-1,4'-piperidin]-3-one using 2-bromo-3-fluorobenzoic acid instead of 2-bromo-5-fluorobenzoic acid, the title compound was obtained as a white solid (20% yield). MS m/e: 312 (M+H$^+$).

b) 1'-Benzyl-7-fluoro-3H-spiro[2-benzofuran-1,4'-piperidine]

Following the procedure described for the synthesis of 1'-benzyl-6-fluoro-3H-spiro[2-benzofuran-1,4'-piperidine], the title compound was obtained as a white solid (82% yield). MS m/e: 298 (M+H$^+$).

c) 7-Fluoro-3H-spiro[2-benzofuran-1,4'-piperidine]

To a solution of 1'-benzyl-6-fluoro-3H-spiro[2-benzofuran-1,4'-piperidine] (1 g, 3.4 mmol) in ethanol (10 ml) was added Pd/C 10% (100 mg, 0.09 mmol). The mixture was refluxed under an hydrogen atmosphere for 8 hours then cooled to room temperature and purged with argon. The catalyst was filtered and the filtrate was concentrated in vacuo to yield 0.67 g (96%) 6-fluoro-3H-spiro[2-benzofuran-1,4'-piperidine] as a white solid. MS m/e: 208 (M+H$^+$).

Amine 4

(RS)-3-Methyl-3H-spiro[2-benzofuran-1,4'-piperidine]

a) (RS)-1-(2-Bromo-phenyl)-ethanol

To a solution of 2'-bromoacetophenone (15 g, 74.6 mmol) in 150 ml MeOH under argon at room temperature was added $NaBH_4$ (4.23 g, 0.11 mol). The reaction mixture was stirred at room temperature for 24 h then quenched by addition of water. HCl 5 N was added until pH 6-7. MeOH was evaporated. The residue was dissolved in ether and washed once with water, once with brine. The organic phase was dried over $Na_2SO_4$ and concentrated in vacuo. The residue was chromatographed on silica gel (eluent: heptane: ethylacetate 1:1) to yield 14.8 g (99%) of (RS)-1-(2-bromo-phenyl)-ethanol as a colorless oil.

b) (RS)-1-Benzyl-4-[2-(1-hydroxy-ethyl)-phenyl]-piperidin-4-ol

To a stirred solution of (RS)-1-(2-bromo-phenyl)-ethanol (8.0 g, 39.8 mmol) −70° C. in tetrahydrofuran (40 ml) was added dropwise a 1.6M n-butyllithium solution in hexane (57.2 ml, 91.5 mmol) over a period of 20 min. After 2 hours, a solution of 1-benzyl-4-piperidone (10.2 ml, 55.7 mmol) in tetrahydrofuran (32 ml) was added dropwise. The mixture was allowed to warm to room temperature and stirred overnight. The mixture was poured into a stirred mixture of water (200 ml) and ether (200 ml). The aqueous layer was extracted with ether (2×100 ml). The combined extracts were washed with water (80 ml), dried over $Na_2SO_4$, filtered and concentrated in vacuo. The crude oil was chromatographed on silica gel (eluent: heptane/ethylacetate 3:7) to yield 6.1 g (49%) of (RS)-1-benzyl-4-[2-(1-hydroxy-ethyl)-phenyl]-piperidin-4-ol as a white solid. MS m/e: 312 (M+H$^+$).

c) (RS)-1'-Benzyl-3-methyl-3H-spiro[2-benzofuran-1,4'-piperidine]

To a solution of (RS)-1-benzyl-4-[2-(1-hydroxy-ethyl)-phenyl]-piperidin-4-ol (3 g, 9.6 mmol) in tetrahydrofuran (30 ml) was added triethylamine (2.95 ml, 21.2 mmol), dimethylaminopyridine (120 mg, 0.96 mmol) and methanesulfonyl-chloride (0.84 ml, 10.6 mmol). The reaction mixture was refluxed for 3 hours, cooled to room temperature, quenched with water (15 ml) and ethylacetate (15 ml). The organic phase was dried over $Na_2SO_4$ and concentrated in vacuo to yield 2.95 g (quant.) of (RS)-1'-benzyl-3-methyl-3H-spiro[2-benzofuran-1,4'-piperidine] as an orange oil. MS m/e: 294 (M+H$^+$).

d) (RS)-3-Methyl-3H-spiro[2-benzofuran-1,4'-piperidine]

Following the procedure described for the synthesis of 6-fluoro-3H-spiro[2-benzofuran-1,4'-piperidine], the title compound was obtained as a colorless oil (72% yield). MS m/e: 204 (M+H$^+$).

Amine 5

3,4-Dihydrospiro[isochromene-1,4'-piperidine]

a) 1-Benzyl-4-[2-(2-hydroxy-ethyl)-phenyl]-piperidin-4-ol

To a solution of 2-bromophenyl ethyl alcohol (1.9 g, 9.6 mmol) in tetrahydrofuran (25 ml) was added 1.6 M n-butyl lithium solution in n-hexane (14 ml, 23 mmol) at –60° C. After stirring for 30 min a solution of 1-benzyl-4-piperidone (2.6 g, 14 mmol) in tetrahydrofuran (10 ml) was added over a period of 15 min at –40° C. The cooling bath was removed and the reaction mixture was stirred for 72 h at room temperature. The mixture was quenched with saturated aqueous ammonium chloride solution (30 ml). Basification to pH 11 with 2 M aqueous sodium carbonate solution (50 ml) was followed by extraction with three 100-ml portions of tert-butyl methyl ether. The combined organic layers were dried over anhydrous sodium sulfate and concentrated in vacuo. Volatile impurities were removed by kugelrohrdistillation at 170° C. and 1-2 mbar. Flash chromatography of the residual crude product with dichloromethane/methanol as eluent gave the title compound (2.3 g, 53%) as dark brown oil. MS m/e: 312 (M+H$^+$).

b) 1'-Benzyl-3,4-dihydrospiro[isochromene-1,4'-piperidine]

To a solution of 1-benzyl-4-[2-(2-hydroxy-ethyl)-phenyl]-piperidin-4-ol (2.0 g, 6.6 mmol) and triethylamine (1.9 ml, 14 mmol) dry tetrahydrofuran (50 ml) was added methanesulfonyl chloride (0.48 ml, 6.2 mmol) at room temperature. The reaction mixture was heated at reflux for 4 h. Quenching with water and basification with 1 M aqueous sodium hydroxide solution was followed by extraction with three portions of ethyl acetate. The combined organic layers were dried over anhydrous sodium sulfate and concentrated in vacuo. Flash chromatography of the crude product with n-heptane/ethyl acetate as eluent gave the title compound (0.40 g, 21%) as yellow oil. MS m/e: 294 (M+H$^+$).

c) 3,4-Dihydrospiro[isochromene-1,4'-piperidine]

A solution of 1'-benzyl-3,4-dihydrospiro[isochromene-1,4'-piperidine] (0.40 g, 1.3 mmol) in ethanol (15 ml) was purged with argon. After addition of the palladium catalyst (10% Pd on activated charcoal, 0.14 g) the reaction vessel was filled with hydrogen gas. The mixture was stirred for 18 h at room temperature. The catalyst was removed by filtration and the filtrate was concentrated in vacuo to give the title compound (0.23 g) as white solid with a purity of approx. 88% as assessed by $^1$H-NMR (contaminated with 1'-ethyl-3,4-dihydrospiro[isochromene-1,4'-piperidine]). MS m/e: 204 (M+H$^+$).

Amine 6

1H-Spiro[isochromene-4,4'-piperidine]

a) (4-Phenyl-piperidin-4-yl)-methanol

To a solution of 4-phenyl-4-piperidinecarboxylic acid 4-toluene-sulfonate (2.0 g, 5.3 mmol) in dry tetrahydrofuran (10 ml) was added 1 M lithium aluminum hydride solution in tetrahydrofuran at 0° C. The reaction mixture was heated at reflux for 90 min. After cooling to 0° C. water (0.4 ml), 2 M aqueous sodium hydroxide solution (0.6 ml) and water (0.8 ml) were added consecutively. The white suspension was stirred for 10 min and diluted with tetrahydrofuran (40 ml). After addition of anhydrous sodium sulfate (18 g) the suspension was stirred for further 10 min. The precipitate was removed by filtration and the filtrate was concentrated in vacuo to give the crude title compound (0.65 g, 64%) as white solid.
MS m/e: 192 (M+H$^+$).

b) 1H-Spiro[isochromene-4,4'-piperidine]

A mixture of (4-phenyl-piperidin-4-yl)-methanol (0.1 g, 0.5 mmol), paraformaldehyde (0.11 g, 3.7 mmol), 1,4-dioxane (5 ml) and concentrated hydrochloric acid solution (1.3 ml) was heated at reflux for 80 h. The reaction mixture was diluted with ethyl acetate (100 ml) and washed with 0.5 M aqueous sodium hydroxide solution. The aqueous layer was extracted with ethyl acetate (100 ml). The combined organic layers were dried over anhydrous sodium sulfate and concentrated in vacuo. Flash chromatography of the crude product with dichloromethane/methanol as eluent gave the title compound (0.053 g, 50%) as yellow solid. MS m/e: 204 (M+H$^+$).

Amine 7

(RS)-3'H-Spiro[azepane-4,1'-[2]benzofuran]

a) (RS)-1-Benzyl-4-(2-hydroxymethyl-phenyl)-azepan-4-ol

To a solution of 2-bromobenzyl alcohol (7.8 g, 42 mmol) in tetrahydrofuran (80 ml) was added dropwise a 2.8 M solution of ethylmagnesium chloride in tetrahydrofuran (15 ml, 42 mmol). The reaction was exothermic, and the rate of addition was adjusted to maintain a gentle reflux. After completed addition magnesium turnings (1.0 g, 42 mmol) were added in portions. The mixture was heated at reflux for 2 h before addition of a solution of 1-benzyl-azepan-4-one (8.5 g, 42 mmol) in tetrahydrofuran (40 ml). The reaction mixture was heated for another 4 h at reflux. Cooling to room temperature was followed by slow addition of saturated ammonium chloride solution (50 ml), water (100 ml) and ethyl acetate (300 ml). The layers were separated, and the organic layer was concentrated to give a green oil. Flash column chromatography using a 2:1 mixture of heptane and ethyl acetate as eluent gave the title compound as a light yellow oil (8.0 g, 61%).

b) (RS)-1-Benzyl-3'H-spiro[azepane-4,1'-[2]benzofuran]

To a solution of (RS)-1-benzyl-4-(2-hydroxymethyl-phenyl)-azepan-4-ol (7.0 g, 22 mmol) and triethylamine (3.1 ml, 22 mmol) in tetrahydrofuran (80 ml) was added a solution of methanesulfonyl chloride (1.7 ml, 22 mmol) in tetrahydrofuran (20 ml) at 0° C. After completed addition the temperature was allowed to rise to room temperature. Stirring for 2 h was followed by addition of another portion of triethylamine (3.1 ml, 22 mmol). Stirring was continued over night. The reaction mixture was partitioned between water and ethyl acetate. The layers were separated and the organic layer was concentrated in vacuo. Flash column chromatography using heptane/ethyl acetate as eluent gave the title compound as a light yellow oil (4.0 g, 61%).

MS m/e: 294 (M+H$^+$).

c) (RS)-3'H-Spiro[azepane-4,1'-[2]benzofuran]

A solution of (RS)-1-benzyl-3'H-spiro[azepane-4,1'-[2] benzofuran] (4.00 g, 13.6 mmol) in methanol (50 ml) in an autoclave was purged with argon. After addition of the palladium catalyst (10% Pd on activated charcoal, 1 g) the autoclave was pressurized with 5 bar of hydrogen gas. The mixture was stirred over night at room temperature. The catalyst was removed by filtration and the filtrate was concentrated in vacuo. The residue was partitioned between ethyl acetate and aqueous sodium hydroxide solution (pH 14). The layers were separated and the aqueous layer was extracted with ethyl acetate. The combined organic layers were dried over sodium sulfate and concentrated in vacuo to give the title compound as white solid (2.5 g, 90%).

MS m/e: 204 (M+H$^+$).

EXAMPLES

General Procedure I

Condensation of Hydrazide and Thiolactam to Triazole

A mixture of a hydrazide derivative of formula (II) (1-1.5 eq) and a thiolactam of formula (III) (1 eq) in n-butanol (0.1-0.2 M) is heated at reflux for 16-72 h. After cooling to room temperature the solvent is evaporated and the residue is purified by flash-chromatography to give an N—BOC derivative of formula (I-1-a). Under the reaction conditions the N—BOC group can be partially or completely cleaved thermally, and a secondary amine derivative of formula (I-1-b) is obtained in addition or as the sole product.

General Procedure II

Cleavage of N—BOC Group

A solution of an N—BOC derivative of general formula (I-a) (1 eq) in 1.25 M methanolic hydrogen chloride solution (10-20 eq HCl) is heated at 50° C. for 15-60 min. After cooling to room temperature the reaction mixture is concentrated in vacuo to give a secondary amine derivative of general formula (I-b) as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula (I-b).

General Procedure III

Reductive N-Alkylation

A mixture of a compound of formula (I-b) as free base or as hydrochloride salt (1 eq, 0.1-0.2 M), triethylamine (1 eq when the hydrochloride salt of a compound of formula (I-b) is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl derivative of formula (I).

Example 1 tert-Butyl 8-chloro-1-[(1r,4'r)-3H-spiro[2-benzofuran-1,1'-cyclohexan]-4'-yl]-4H-[1,2,4]triazolo[4,3-a][1,4]benzodiazepine-5(6H)-carboxylate The title compound was obtained as white foam in 65% yield according to general procedure I. Hydrazide: (1r,4'r)-3H-Spiro[2-benzofuran-1,1s-cyclohexane]-4'-carboxylic acid. Thiolactam: 7-Chloro-2-thioxo-1,2,3,5-tetrahydrobenzo[e][1,4]diazepine-4-carboxylic acid tert-butyl ester. MS m/e: 507 (M+H$^+$)

Example 2

8-Chloro-1-[(1r,4'r)-3H-spiro[2-benzofuran-1,1'-cyclohexan]-4'-yl]-5,6-dihydro-4H-[1,2,4]triazolo[4,3-a][1,4]benzodiazepine hydrochloride The title compound was obtained as white solid in quantitative yield from tert-butyl 8-chloro-1-[(1r,4'r)-3H-spiro[2-benzofuran-1,1'-cyclohexan]-4'-yl]-4H-[1,2,4]triazolo[4,3-a][1,4]benzodiazepine-5(6H)-carboxylate according to general procedure II.
MS m/e: 407 (M+H$^+$)

Example 3

8-Chloro-5-methyl-1-[(1r,4'r)-3H-spiro[2-benzofuran-1,1'-cyclohexan]-4'-yl]-5,6-dihydro-4H-[1,2,4]triazolo[4,3-a][1,4]benzodiazepine The title compound was obtained as white solid in 84% yield from 8-chloro-1-[(1r,4'r-3H-spiro[2-benzofuran-1,1'-cyclohexan]-4'-yl]-5,6-dihydro-4H-[1,2,4]triazolo[4,3-a][1,4]benzodiazepine hydrochloride and paraformaldehyde according to general procedure III.
MS m/e: 421 (M+H$^+$).

Example 4 tert-Butyl 8-chloro-1-[(1s,4's)-3H-spiro[2-benzofuran-1,1'-cyclohexan]-4'-yl]-4H-[1,2,4]triazolo[4,3-a][1,4]benzodiazepine-5(6H)-carboxylate The title compound was obtained as white foam in 60% yield according to general procedure I. Hydrazide: (1 s,4's)-3H-Spiro[2-benzofuran-1,1'-cyclohexane]-4'-carbohy-

Example 5

8-Chloro-1-[(1s,4's)-3H-spiro[2-benzofuran-1,1'-cyclohexan]-4'-yl]-5,6-dihydro-4H-[1,2,4]triazolo[4,3-a][1,4]benzodiazepine hydrochloride The title compound was obtained as white solid in quantitative yield from tert-butyl 8-chloro-1-[(1s,4's)-3H-spiro[2-benzofuran-1,1'-cyclohexan]-4'-yl]-4H-[1,2,4]triazol[4,3-a][1,4]benzodiazepine-5(6H)-carboxylate according to general procedure II.
MS m/e: 407 (M+H$^+$).

Example 6

8-Chloro-5-methyl-1-[(1s,4's)-3H-spiro[2-benzofuran-1,1'-cyclohexan]-4'-yl]-5,6-dihydro-4H-[1,2,4]triazolo[4,3-a][1,4]benzodiazepine The title compound was obtained as white solid in 77% yield from 8-chloro-1-[(1s,4's)-3H-spiro[2-benzofuran-1,1'-cyclohexan]-4'-yl]-5,6-dihydro-4H-[1,2,4]triazolo[4,3-a][1,4]benzodiazepine hydrochloride and paraformaldehyde according to general procedure III.
MS m/e: 421 (M+H$^+$).

Example 7 tert-Butyl 8-chloro-1-(1'H,3H-spiro[2-benzofuran-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (1.00 g, 2.50 mmol) and 3H-spiro[2-benzofuran-1,4'-piperidine] (1.89 g, 10.0 mmol) were smelted over night at 130° C. After cooling to room temperature, the mixture was suspended with ethyl acetate and filtered. The filtrate was concentrated in vacuo. Chromatography on silica gel with ethyl acetate yielded 0.38 g (30%) tert-butyl 8-chloro-1-(1'H,3H-spiro[2-benzofuran-1,4'-piperidin]-1'-yl)-4H-[1,2,4]triazolo[4,3-a][1,4]benzodiazepine-5(6H)-carboxylate as slight yellow solid. MS m/e: 508 (M+H$^+$).

Example 8

8-Chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride The title compound was obtained as light yellow solid in quantitative yield from tert-butyl 8-chloro-1-(1'H,3H-spiro[2-benzofuran-1,4'-piperidin]-1'-yl)-4H-[1,2,4]triazolo[4,3-a][1,4]benzodiazepine-5(6H)-carboxylate according to general procedure II.
MS m/e: 408 (M+H$^+$).

Example 9

8-Chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine To a suspension of 8-chloro-1-(1'H,3H-spiro[2-benzofuran-1,4'-piperidin]-1'-yl)-5,6-dihydro-4H[1,2,4]triazolo[4,3-a][1,4]benzodiazepine hydrochloride (38 mg, 0.086 mmol) in methanol (1.2 ml) were added triethylamine (18 µl, 0.13 mmol) and paraformaldehyde (22 mg, 0.68 mmol). The mixture was heated at reflux for 2 h. After cooling on an ice bath sodium cyanoborohydride (10 mg, 0.128 mmol) was added. The mixture was stirred at room temperature for 1 h, quenched with water, diluted with 1 M aqueous sodium hydroxide solution and extracted with three portions of ethyl acetate. The combined extracts were dried over Na$_2$SO$_4$, filtered and concentrated in vacuo. The crude material was purified by chromatography on silica gel (2 g Flashpack cartridge, eluent: ethylacetate then ethylacetate: methanol 9:1) to yield 21 mg (58%) of 8-chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine as white foam. MS m/e: 422 (M+H$^+$).

Example 10

8-Chloro-5-isopropyl-1-(1'H,3H-spiro[2-benzofuran-1,4'-piperidin]-1'-yl)-5,6-dihydro-4H-[1,2,4]triazolo[4,3-a][1,4]benzodiazepine To a solution of 8-chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride (50 mg, 0.12 mmol) in 2 acetonitrile and 1 ml dichloromethane were added acetone (50 µl, 0.68 mmol) and sodium triacetoxyborohydride (43 mg, 0.20 mmol). The reaction mixture was stirred at room temperature for 2 days and the solvent was removed by distillation. Chromatography (10 g silica gel, dichloromethane/methanol, 95:5 to 8:2) yielded 21 mg (38%) 8-chloro-5-isopropyl-1-(1'H,3H-spiro[2-benzofuran-1,4'-piperidin]-1'-yl)-5,6-dihydro-4H-[1,2,4]triazolo[4,3-a][1,4]benzodiazepine as colorless oil. MS m/e: 450 (M+H$^+$).

Example 11

2-[8-Chloro-1-(1'H,3H-spiro[2-benzofuran-1,4'-piperidin]-1'-yl)-4H-[1,2,4]triazolo[4,3-a][1,4]benzodiazepin-5(6H)-yl]ethanol 8-Chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride (0.10 g, 0.25 mmol) and glycolaldehyde (0.15 g, 0.25 mmol) in 1 ml dichloromethane were stirred at room temperature for 2 h. Formic acid (37.4 µl, 0.98 mmol) and sodium cyanoborohydride (16.2 mg, 0.25 mmol) were added. The reaction mixture was stirred at room temperature over night, then 50 ml 0.1 N aqueous sodium hydroxide solution were added. Extraction with dichloromethane and chromatography (-a: 20 g silica gel, dichloromethane/methanol, -b: 10 g silica gel ethyl acetate/heptane, -c: 5 g silica gel, dichloromethane/methanol and -d: 10 g Flasch-NH$_2$ Isolute column, ethyl acetate) yielded 3.5 mg (3%) 2-[8-chloro-1-(1'H,3H-spiro[2-benzofuran-1,4'-piperidin]-1'-yl)-4H-[1,2,4]triazole[4,3-a][1,4]benzodiazepin-5(6H)-yl]ethanol as white solid. MS m/e: 452 (M+H$^+$).

Example 12

8-Chloro-5-(pyridin-2-ylmethyl)-1-(1'H,3H-spiro[2-benzofuran-1,4'-piperidin]-1'-yl)-5,6-dihydro-4H-[1,2,4]triazolo[4,3-a][1,4]benzodiazepine 8-Chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride (100 mg, 0.25 mmol), 2-picolyl chloride hydrochloride (45 mg, 0.27 mmol) and N-ethyldiisopropylamine (47.1 μl, 0.27 mmol) in 2 ml dimethyl formamide were stirred over night at 50° C. Then another portion of 2-picolyl chloride hydrochloride (100 mg) was added and stirring was continued at 50° C. over night. 2-(Bromomethyl)pyridine hydrobromide (100 mg) and N-ethyldiisopropylamine (0.10 ml) were added and the mixture was stirred over night at 50° C. The solvent was removed and the residue was purified by chromatography (first chromatography on 20 g Flash-NH$_2$ Isolute column, ethyl acetate, second chromatography on 20 g silica gel, ethyl acetate/methanol) to yield 49 mg (40%) 8-chloro-5-(pyridin-2-ylmethyl)-1-(1'H,3H-spiro[2-benzofuran-1,4'-piperidin]-1'-yl)-5,6-dihydro-4H-[1,2,4]triazolo[4,3-a][1,4]benzodiazepine as white solid. MS m/e: 499 (M+H$^+$).

Example 13

8-Chloro-N,N-dimethyl-1-(1'H,3H-spiro[2-benzofuran-1,4'-piperidin]-1'-yl-4H-[1,2,4]triazolo[4,3-a][1,4]benzodiazepine-5(6H)-sulfonamide A mixture of 8-chloro-1-(1'H,3H-spiro[2-benzofuran-1,4'-piperidin]-1'-yl)-5,6-dihydro-4H-[1,2,4]triazolo[4,3-a][1,4] benzodiazepine hydrochloride (50.0 mg, 0.12 mmol), dimethylsulfamoyl chloride (13.3 μl, 0.12 mmol) and pyridine (9.9 μl, 0.123 mmol) dissolved in 2 ml dichloromethane were stirred over night at 40° C. The solvent was removed by distillation and the residue was purified by chromatography (20 g silica gel, ethyl acetate/methanol) to yield 35 mg (55%) 8-chloro-N,N-dimethyl-1-(1'H,3H-spiro[2-benzofuran-1,4'-piperidin]-1'-yl)-4H-[1,2,4]triazolo[4,3-a][1,4]benzodiazepine-5(6H)-sulfonamide as white solid.
MS m/e: 515 (M+H$^+$).

Example 14

Methyl 8-chloro-1-(1'H,3H-spiro[2-benzofuran-1,4'-piperidin]-1'-yl)-4H-[1,2,4]triazolo[4,3-a][1,4]benzodiazepine-5(6H)-carboxylate 8-Chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride (100 mg, 0.25 mmol), triethylamine (85.8 μl, 0.61 mmol), methyl chloroformate (21 μl, 0.27 mmol) and 4-N,N-dimethylaminopyridine (3 mg, 24.5 mmol) in 2 ml dichloromethane were stirred at room temperature for 1 h. The reaction mixture was added to saturated aqueous sodium hydrogen carbonate solution. Extraction with ethyl acetate, removal of the solvent by distillation and chromatography (10 g SiO$_2$, dichloromethane/methanol) yielded 76 mg (66%) methyl 8-chloro-1-(1'H-1,3H-spiro[2-benzofuran-1,4'-piperidin]-1'-yl)-4H-[1,2,4]triazolo[4,3-a][1,4]benzodiazepine-5(6H)-carboxylate as white solid. MS m/e: 466 (M+H$^+$).

Example 15

5-Acetyl-8-chloro-1-(1'H,3H-spiro[2-benzofuran-1,4'-piperidin]-1'-yl-5,6-dihydro-4H-[1,2,4]triazolo[4,3-a][1,4]benzodiazepine A mixture of 8-chloro-1-(1'H-3H-spiro[2-benzofuran-1,4'-piperidin]-1'-yl)-5,6-dihydro-4H-[1,2,4]triazolo[4,3-a][1,4]benzodiazepine hydrochloride (75 mg, 0.18 mmol) and acetyl chloride (66 μl, 0.92 mmol). in dichloromethane was stirred over the weekend at room temperature. The solvent was removed by distillation and the residue was purified by chromatography (10 g silica gel, dichloromethane/methanol 8:2). The resulting substance was suspended in 0.1 M aqueous sodium hydroxide solution and extracted with ethyl acetate and dichloromethane to yield 49 mg (59%) 5-acetyl-8-chloro-1-(1'H,3H-spiro[2-benzofuran-1,4'-piperidin]-1'-yl)-5,6-dihydro-4H-[1,2,4]triazolo[4,3-a][1,4]benzodiazepine as light yellow solid,
MS m/e: 450 (M+H$^+$).

Example 16

2-[8-Chloro-1-(1'H,3H-spiro[2-benzofuran-1,4'-piperidin]-1'-yl)-4H-[1,2,4]triazolo[4,3-a][1,4]benzodiazepin-5(6H)-yl]-N,N-dimethyl-2-oxoethanamine A mixture of 8-chloro-1-(1'H,3H-spiro[2-benzofuran-1,4]-piperidin)-1'-yl)-5,6-dihydro-4H-[1,2,4]triazolo[4,3-a][1,4]benzodiazepine (0.30 g, 0.74 mmol), N-ethyldiisopropylamine (0.51 ml, 2.94 mmol) and dimethylaminoacetyl chloride hydrochloride (0.21 g, 1.10 mmol) in 12 ml THF were stirred at room temperature over night. Extraction with ethyl acetate and chromatography (20 g Flash-NH2 Isolute column, ethyl acetate) yielded 93 mg (26%) 2-[8-chloro-1-(1'H,3H-spiro[2-benzofuran-1,4'-piperidin]-1'-yl)-4H-[1,2,4]triazolo[4,3-a][1,4]benzodiazepin-5(6H)-yl]-N,N-dimethyl-2-oxoethanamine as white solid.
MS m/e: 493 (M+H$^+$).

Example 17 tert-Butyl 8-chloro-1-(6-fluoro-1'H,3H-spiro[2-benzofuran-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.16 g, 0.4 mmol) and 6-fluoro-3H-spiro[2-benzofuran-1,4'-piperidine] (0.36 g, 1.76 mmol) was heated at 130° C. for 3 hours. After cooling, the mixture was suspended with ethyl acetate and filtered. Chromatography on silica gel with ethyl acetate yielded 0.11 g (52%) of tert-butyl 8-chloro-1-(6-fluoro-1'H,3H-spiro[2-benzofuran-1,4'-piperidin]-1'-yl)-4H-[1,2,4]triazolo[4,3-a][1,4]benzodiazepine-5(6H)-carboxylate as slight yellow foam.
MS m/e: 526 (M+H$^+$).

Example 18

8-Chloro-1-(6-fluoro-1'H-3H-spiro[2-benzofuran-1,4'-piperidin]-1'-yl)-5,6-dihydro-4H-[1,2,4]triazolo[4,3-a][1,4]benzodiazepine hydrochloride The title compound was obtained as white foam in quantitative yield from tert-butyl 8-chloro-1-(6-fluoro-1'H,3H-spiro[2-benzofuran-1,4'-piperidin]-1'-yl)-4H-[1,2,4]triazolo[4,3-a][1,4]benzodiazepine-5(6H)-carboxylate according to general procedure II.
MS m/e: 426 (M+H$^+$).

Example 19

8-Chloro-1-(6-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine The title compound was obtained as off-white solid in 88% yield from 8-chloro-1-(6-fluoro-1'H,3H-spiro[2-benzofuran- 1,4'-piperidin]-1'-yl)-5,6-dihydro-4H-[1,2,4]triazolo[4,3-a][1,4]benzodiazepine hydrochloride and paraformaldehyde according to general procedure III.

MS m/e: 440 (M+H$^+$).

Example 20 tert-Butyl 8-chloro-1-(7-fluoro-1'H,3H-spiro[2-benzofuran-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.16 g, 0.4 mmol) and 7-fluoro-3H-spiro[2-benzofuran-1,4'-piperidine] (0.33 g, 1.6 mmol) was heated at 130° C. for 2 hours. After cooling to room temperature, the mixture was suspended with ethyl acetate and filtered. Chromatography on silica gel with ethyl acetate yielded 0.15 g (69%) of tert-butyl 8-chloro-1-(7-fluoro-1'H,3H-spiro[2-benzofuran-1,4'-piperidin]-1'-yl)-4H-[1,2,4]triazolo[4,3-a][1,4]benzodiazepine-5(6H)-carboxylate as light yellow foam. MS m/e: 526 (M+H$^+$).

Example 21

8-Chloro-1-(7-fluoro-1'H,3H-spiro[2-benzofuran-1,4'-piperidin]-1'-yl)-5,6-dihydro-4H-[1,2,4]triazolo[4,3-a][1,4]benzodiazepine hydrochloride The title compound was obtained as white foam in quantitative yield from tert-butyl 8-chloro-1-(7-fluoro-1'H,3H-spiro[2-benzofuran-1,4'-piperidin]-1'-yl)-4H-[1,2,4]triazolo[4,3-a][1,4]benzodiazepine-5(6H)-carboxylate according to general procedure II.

MS m/e: 426 (M+H$^+$).

Example 22

8-Chloro-1-(7-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine The title compound was obtained as off-white solid in 76% yield from 8-chloro-1-(7-fluoro-1'H-1,3H-spiro[2-benzofuran-1,4'-piperidin]-1'-yl-5,6-dihydro-4H-[1,2,4]triazolo[4,3-a][1,4]benzodiazepine hydrochloride and paraformaldehyde according to general procedure III.

MS m/e: 440 (M+H$^+$).

Example 23

8-Chloro-1-(5-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine A mixture of 1-bromo-8-chloro-5-methyl-5,6-dihydro-4H-2,3,5,10b-tetraaza-benzoazulene (50 mg, 0.16 mmol), tetrabutylammonium bromide (10 mg, 0.031 mmol) and 5-fluoro-3H-spiro[2-benzofuran-1,4'-piperidine] (66 mg, 0.32 mmol) in sulfolane (0.5 ml) was stirred at 160° C. for 20 h. The solvent was removed by kugelrohrdistillation (140° C., 1-2 mbar). Flash chromatography over aminopropyl-modified silica gel with n-heptane/ethyl acetate and further purification by preparative HPLC with n-heptane/2-propanol (70:30) as eluent gave the title compound (9 mg, 13%) as white solid. MS m/e: 440 (M+H$^+$).

Example 24

(RS)-tert-Butyl 8-chloro-1-(3-methyl-1'H,3H-spiro[2-benzofuran-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.16 g, 0.4 mmol) and (RS)-3-methyl-3-spiro[2-benzofuran-1,4'-piperidine] (0.32 g, 1.6 mmol) was heated at 130° C. for 3 hours. After cooling to room temperature, the mixture was suspended with ethyl acetate and filtered. Chromatography on silica gel with ethyl acetate yielded 0.076 g (36%) of (RS)-tert-butyl 8-chloro-1-(3-methyl-1'H,3H-spiro[2-benzofuran-1,4'-piperidin]-1'-yl)-4H-[1,2,4]triazolo[4,3-a][1,4]benzodiazepine-5(6H)-carboxylate as slight brown foam MS m/e: 522 (M+H$^+$),

Example 25

(RS)-8-Chloro-1-(3-methyl-1'H,3H-spiro[2-benzofuran-1,4'-piperidin]-1'-yl)-5,6-dihydro-4H-[1,2,4]triazolo[4,3-a][1,4]benzodiazepine hydrochloride The title compound was obtained as off-white solid in quantitative yield from (RS)-tert-butyl 8-chloro-1-(3-methyl-1'H-1,3H-spiro[2-benzofuran-1,4'-piperidin]-1'-yl)-4H-[1,2,4]triazolo[4,3-a][1,4]benzodiazepine-5(6H)-carboxylate according to general procedure II.

MS m/e: 422 (M+H$^+$).

Example 26

(RS)-8-Chloro-5-methyl-1-(3-methyl-1'H,3H-spiro[2-benzofuran-1,4'-piperidin]-1'-yl)-5,6-dihydro-4H-[1,2,4]triazolo[4,3-a][1,4]benzodiazepine The title compound was obtained as white solid in 25% yield from (RS)-8-chloro-1-(3-methyl-1'H,3H-spiro[2-benzofuran-1,4'-piperidin]-1'-yl)-5,6-dihydro-4H-[1,2,4]triazolo[4,3-a][1,4]benzodiazepine hydrochloride and paraformaldehyde according to general procedure III.

MS m/e: 436 (M+H$^+$).

Example 27

1'-(8-Chloro-5-methyl-5,6-dihydro-4H-[1,2,4]triazolo[4,3-a][1,4]benzodiazepin-1-yl)-3H-spiro[2-benzofuran-1,4'-piperidin]-3-one A mixture of 1-bromo-8-chloro-5-methyl-5,6-dihydro-4H-2,3,5,10b-tetraaza-benzoazulene (50 mg, 0.16 mmol), tetrabutylammonium bromide (10 mg, 0.031 mmol) and 3H-spiro[2-benzofuran-1,4'-piperidin]-3-one (65 mg, 0.32 mmol) in sulfolane (0.5 ml) was stirred for 20 h at 160° C. The reaction mixture was poured on water and extracted with tert-butyl methyl ether. The organic layer was washed with water, dried over anhydrous sodium sulfate and concentrated in vacuo. Residual sulfolane was evaporated by kugelrohrdistillation (120° C., 1-2 mbar). Preparative HPLC with n-heptane/2-propanol (70:30) as eluent gave the title compound (10 mg, 14%) as light yellow solid. MS m/e: 436 (M+H$^+$).

Example 28

8-Chloro-1-(1'H,3H-spiro[2-benzothiophene-1,4'-piperidin]-1'-yl)-5,6-dihydro-4H-[1,2,4]triazolo[4,3-a][1,4]benzodiazepine a) tert-Butyl 8-chloro-1-(1'H,3H-spiro[2-benzothiophene-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.3 g, 0.75 mmol) and 3H-spiro[2-benzothiophene-1,4'-piperidine] (1.5 g, 7.5 mmol) was stirred at 140° C. for 24 h. The reaction mixture was transferred directly onto a flash chromatography column filled with aminopropyl modified silica gel and eluted with n-heptane/ethyl acetate give crude tert-butyl 8-chloro-1-(1'H,3H-spiro[2-benzothiophene-1,4'-piperidin]-1'-yl)-4H-[1,2,4]triazolo[4,3-a][1,4]benzodiazepine-5(6H-carboxylate (0.11 g, 27%) as yellow oil, which was used in the next step without further purification.

b) 8-Chloro-1-(1'H,3H-spiro[2-benzothiophene-1,4'-piperidin]-1'-yl)-5,6-dihydro-4H-[1,2,4]triazolo[4,3-a][1,4]benzodiazepine A solution of the crude tert-butyl 8-chloro-1-(1'H,3H-spiro[2-benzothiophene-1,4'-piperidin]-1'-yl)-4H-[1,2,4]triazolo[4,3-a][1,4]benzodiazepine-5(6H)-carboxylate (0.092 g, ca. 0.18 mmol) from the previous step in 1.25 M methanolic hydrogen chloride solution (1.4 ml, 1.8 mmol) was heated at 50° C. for 3 h. The reaction mixture was poured on 1 M aqueous sodium hydroxide solution (30 ml) and extracted with ethyl acetate (2×30 ml). The combined organic layers were dried over anhydrous sodium sulfate and concentrated in vacuo. Flash chromatography over aminopropyl modified silica gel with n-heptane/ethyl acetate as eluent gave the title compound (0.045 g, 60%) as white solid. MS m/e: 424 (M+H$^+$).

Example 29

8-Chloro-5-methyl-1-(1'H,3H-spiro[2-benzothiophene-1,4'-piperidin]-1'-yl-5,6-dihydro-4H-[1,2,4]triazolo[4,3-a][1,4]benzodiazepine A mixture of 8-chloro-1-(1'H-3H-spiro[2-benzothiophene-1,4'-piperidin]-1'-yl)-5,6-dihydro-4H-[1,2,4]triazolo[4,3-a][1,4]benzodiazepine (0.041 g, 0.097 mmol) and paraformaldehyde (0.023 g, 0.77 mmol) in methanol (1 ml) was heated at reflux for 5 h. After cooling to room temperature sodium cyanoborohydride (0.012 g, 0.19 mmol) was added at 0° C. The reaction mixture was allowed to warm to room temperature and stirred for 18 h. Quenching with 1 M aqueous sodium hydroxide solution (30 ml) was followed by extraction with ethyl acetate. The organic layer was dried over anhydrous sodium sulfate and concentrated in vacuo. Flash chromatography over aminopropyl modified silica gel with n-heptane/ethyl acetate as eluent gave the title compound (0.020 g, 48%) as off-white solid. MS m/e: 438 (M+H$^+$).

Example 30

8-Chloro-1-(2,2-dioxido-1'H,3H-spiro[2-benzothiophene-1,4'-piperidin]-1'-yl)-5,6-dihydro-4H-[1,2,4]triazolo[4,3-a][1,4]benzodiazepine a) tert-Butyl 8-chloro-1-(2,2-dioxido-1'H,3H-spiro[2-benzothiophene-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.3 g, 0.75 mmol) and 3H-spiro[2-benzothiophene-1,4'-piperidine]2,2-dioxide (1.8 g, 7.5 mmol) was stirred for 24 h at 140° C. The reaction mixture was loaded directly onto Si(CH$_2$)$_3$NH$_2$-silica gel and chromatographed with n-heptane/ethyl acetate as eluent to give crude tert-butyl 8-chloro-1-(2,2-dioxido-1'H-3H-spiro[2-benzothiophene-1,4'-piperidin]-1'-yl)-4H-[1,2,4]triazolo[4,3-a][1,4]benzodiazepine-5(6H)-carboxylate (0.13 g, 31%) as yellow oil, which was used in the next step without further purification.

b) 8-Chloro-1-(2,2-dioxido-1'H,3H-spiro[2-benzothiophene-1,4'-piperidin]-1'-yl)-5,6-dihydro-4H-[1,2,4]triazolo[4,3-a][1,4]benzodiazepine A solution of the crude tert-butyl 8-chloro-1-(2,2-dioxido-1'H,3H-spiro[2-benzothiophene-1,4'-piperidin]-1'-yl)-4H-[1,2,4]triazolo[4,3-a][1,4]benzodiazepine-5(6H)-carboxylate (0.11 g, ca. 0.20 mmol) from the previous step in 1.25 M methanolic hydrogen chloride solution (1.6 ml, 2.0 mmol) was heated at 50° C. for 3 h. The reaction mixture was poured on 1 M aqueous sodium hydroxide solution (30 ml) and extracted with two 30-ml portions of ethyl acetate. The combined organic layers were dried over anhydrous sodium sulfate and concentrated in vacuo. Flash chromatography over aminopropyl modified silica gel with n-heptane/ethyl acetate as eluent gave the title compound (0.036 g, 32%) as white solid. MS m/e: 456 (M+H$^+$).

Example 31

8-Chloro-1-(2,2-dioxido-1'H,3H-spiro[2-benzothiophene-1,4'-piperidin]-1'-yl)-5-methyl-5,6-dihydro-4H-[1,2,4]triazolo[4,3-a][1,4]benzodiazepine A mixture of 8-chloro-1-(2,2-dioxido-1'H-3H-spiro[2-benzothiophene-1,4'-piperidin]-1'-yl-5,6-dihydro-4H-[1,2,4]triazolo[4,3-a][1,4]benzodiazepine (0.032 g, 0.070 mmol) and paraformaldehyde (0.017 g, 0.57 mmol) in methanol (1 ml) was heated at reflux for 5 h. After cooling to room temperature sodium cyanoborohydride (0.009 g, 0.14 mmol) was added at 0° C.

The reaction mixture was allowed to warm to room temperature and stirred for 18 h. Quenching with 1 M aqueous sodium hydroxide solution (30 ml) was followed by extraction with ethyl acetate. The organic layer was dried over anhydrous sodium sulfate and concentrated in vacuo. Flash chromatography over aminopropyl modified silica gel with n-heptane/ethyl acetate as eluent gave the title compound (0.011 g, 26%) as off-white solid. MS m/e: 470 (M+H$^+$).

Example 32

1'-(8-Chloro-5-methyl-5,6-dihydro-4H-[1,2,4]triazolo[4,3-a][1,4]benzodiazepin-1-yl)-1H-spiro[isochromene-4,4'-piperidine]

a) 1'-(8-Chloro-5,6-dihydro-4H-[1,2,4]triazolo[4,3-a][1,4]benzodiazepin-1-yl)-1H-spiro[isochromene-4,4'-piperidine]

A mixture of 1-bromo-8-chloro-4H,6H-2,3,5,10b-tetraaza-benzo[e]azulene-5-carboxylic acid tert-butyl ester (0.25 g, 0.63 mmol) and 1H-spiro[isochromene-4,4'-piperidine] (0.51 g, 2.5 mmol) in sulfolane (5 ml) was stirred for 74 h at 140° C. The solvent was evaporated by kugelrohrdistillation (150° C., 1-2 mbar). After addition of 1.25 M methanolic hydrogen chloride solution (5.0 ml, 6.3 mmol) the mixture was heated at 50° C. for 2 h. The mixture was allowed to cool to room temperature, treated with 1 M aqueous sodium hydroxide solution (30 ml) and extracted with four 30-ml portions of ethyl acetate. The combined organic layers were dried over anhydrous sodium sulfate and concentrated in vacuo. Flash chromatography over aminopropyl modified silica gel with n-heptane/ethyl acetate as eluent gave 1'-(8-chloro-5,6-dihydro-4H-[1,2,4]triazolo[4,3-a][1,4]benzodiazepin-1-yl)-1H-1-spiro[isochromene-4,4'-piperidine] (0.13 g) as brown solid with a purity of 80%, which was used without further purification in the next step.

MS m/e: 422 (M+H$^+$).

b) 1'-(8-Chloro-5-methyl-5,6-dihydro-4H-[1,2,4]triazolo[4,3-a][1,4]benzodiazepin-1-yl)-1H-spiro[isochromene-4,4'-piperidine]

A mixture of the crude 1'-(8-chloro-5,6-dihydro-4H-[1,2,4]triazolo[4,3-a][1,4]benzodiazepin-1-yl)-1H-spiro[isochromene-4,4'-piperidine] (0.10 g, 0.24 mmol) and paraformaldehyde (0.057 g, 1.9 mmol) in methanol (2 ml) was heated at reflux for 4 h. After cooling to room temperature sodium cyanoborohydride (0.03 g, 0.47 mmol) was added at 0° C. The reaction mixture was allowed to warm to room temperature and stirred for 18 h. Quenching with 1 M aqueous sodium hydroxide solution (30 ml) was followed by extraction with ethyl acetate.

The organic layer was dried over anhydrous sodium sulfate and concentrated in vacuo. Flash chromatography over aminopropyl modified silica gel with n-heptane/ethyl acetate as eluent gave the title compound (0.047 g, 45%) as yellow solid. MS m/e: 436 (M+H$^+$).

Example 33 tert-Butyl 8-chloro-1-(3,4-dihydro-1'H-spiro[isochromene-1,4'-piperidin]-1'-yl)-4H-[1,2,4]triazolo[4,3-a][1,4]benzodiazepine-5(6H)-carboxylate A mixture of 1-bromo-8-chloro-4H,6H-2,3,5,10b-tetraaza-benzo[e]azulene-5-carboxylic acid tert-butyl ester (0.72 g, 0.18 mmol) and 3,4-dihydrospiro[isochromene-1,4'-piperidine] (0.11 g, 0.54 mmol) was stirred for 72 h at 130° C. The reaction mixture was poured on water (50 ml) and extracted with three 50-ml portions of ethyl acetate. The combined organic layers were washed with brine, dried over anhydrous sodium sulfate and concentrated in vacuo. Flash chromatography over aminopropyl modified silica gel with n-heptane/2-propanol as eluent gave the title compound (0.062 g, 66%) as white solid. MS m/e: 522 (M+H$^+$).

Example 34

1'-(8-Chloro-5,6-dihydro-4H-[1,2,4]triazolo[4,3-a][1,4]benzodiazepin-1-yl)-3,4-dihydrospiro[isochromene-1,4'-piperidine]hydrochloride The title compound was obtained as off-white solid in 88% yield from tert-butyl 8-chloro-1-(3,4-dihydro-1'H-spiro[isochromene-1,4'-piperidin]-1'-yl)-4H-[1,2,4]triazolo[4,3-a][1,4]benzodiazepine-5(6H)-carboxylate according to general procedure II.

MS m/e: 422 (M+H$^+$).

Example 35

1'-(8-Chloro-5-methyl-5,6-dihydro-4H-[1,2,4]triazolo[4,3-a][1,4]benzodiazepin-1-yl)-3,4-dihydrospiro[isochromene-1,4'-piperidine]

The title compound was obtained as white solid in 50% yield from 1'-(8-chloro-5,6-dihydro-4H-[1,2,4]triazolo[4,3-a][1,4]benzodiazepin-1-yl)-3,4-dihydrospiro[isochromene-1,4'-piperidine]hydrochloride and paraformaldehyde according to general procedure III MS m/e: 436 (M+H$^+$).

Example 36

(+)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran]

and

Example 37

(−)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran]

a) (RS)-1-(8-Chloro-5,6-dihydro-4H-[1,2,4]triazolo[4,3-a][1,4]benzodiazepin-1-yl)-3'H-spiro azepane-4,1'-[2)benzofuran]

A mixture of 1-bromo-8-chloro-4H,6H-2,3,5,10b-tetraaza-benzo[e]azulene-5-carboxylic acid tert-butyl ester (0.2 g, 0.5 mmol) and (RS)-3'H-spiro[azepane-4,1'-[2]benzofuran] (0.31 g, 1.5 mmol) was stirred at 130° C. for 24 h and at 160° C. for 5 h. Another portion of (RS)-3'H-spiro[azepane-4,1'-[2]benzofuran] (0.38 g, 0.19 mmol) was added, and the reaction mixture was stirred at 160° C. for 18 h. The reaction mixture was allowed to cool to room temperature. After addition of 1.25 M methanolic hydrogen chloride solution (4.0 ml, 5.0 mmol) the mixture was heated at 50° C. for 30 min. The mixture was allowed to cool to room temperature, treated with 1 M aqueous sodium hydroxide solution (50 ml) and extracted with two 50-ml portions of dichloromethane. The combined organic layers were dried over anhydrous sodium sulfate and concentrated in vacuo. Flash chromatography with dichloromethane/methanol as eluent gave the title compound (0.23 g) as yellow solid with a purity of 90%. MS m/e: 422 (M+H$^+$).

b) (RS)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran]

The title compound was obtained as off-white solid in 56% yield from (RS)-1-(8-chloro-5,6-dihydro-4H-[1,2,4]triazolo[4,3-a][1,4]benzodiazepin-1-yl)-3'H-spiro[azepane-4,1'-[2]benzofuran] and paraformaldehyde according to general procedure III. MS m/e: 436 (M+H$^+$).

c) (+)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran]

and d) (−)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran]

(+)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran] and (−)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran] were obtained by chiral HPLC separation of (RS)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran] (0.116 g, 0.266 mmol) on a Chiralpak AD column with n-heptane/ethanol (3:1) as eluent.

(+)-1-(8-Chloro-5-methyl-5,6-dihydro-4H-[1,2,4]triazolo[4,3-a][1,4]benzodiazepin-1-yl)-3'H-spiro[azepane-4,1'-[2]benzofuran] (0.036 g, 31%) was obtained as light yellow solid. (MS m/e: 436 (M+H$^+$)).(−)-1-(8-Chloro-5-methyl-5,6-dihydro-4H-[1,2,4]triazolo[4,3-a][1,4]benzodiazepin-1-yl)-3'H-spiro[azepane-4,1'-[4]benzofuran] (0.037 g, 32%) was obtained as light yellow solid. (MS m/e: 436 (M+H$^+$), $[\alpha]_D$=−17.8 (c=0.141, CHCl$_3$, 20° C.).

The invention claimed is:
1. A compound of formula (I)

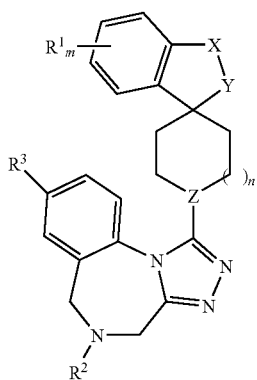

I wherein
X—Y is C(R$^a$R$^b$)—O, wherein R$^a$ and R$^b$ are each independently H or C$_{1-4}$-alkyl,
C(R$^c$R$^d$)—S(O)$_p$, wherein R$^c$ and R$^d$ are each independently H or C$_{1-4}$-alkyl,
C(O)O,
CH$_2$OCH$_2$, or
CH$_2$CH$_2$O;

Z is CH or N;
R$^1$ is halo, cyano, C$_{1-4}$-alkoxy, or C$_{1-4}$-alkyl;
R$^2$ is H,
C$_{1-12}$-alkyl, unsubstituted or substituted with one or more OH, halo, cyano or C$_{1-12}$-alkoxy,
—(CH$_2$)$_q$—R$^e$, wherein R$^e$ is phenyl or 5- or 6-membered heteroaryl, each unsubstituted or substituted with one or more substituents independently selected from A,
—(CH$_2$)$_r$NR$^i$R$^{ii}$,
—C(O)—C$_{1-12}$-alkyl, wherein C$_{1-12}$-alkyl is unsubstituted or substituted with one or more OH, halo, cyano or C$_{1-12}$-alkoxy,
—C(O)(CH$_2$)$_q$OC(O)—C$_{1-12}$-alkyl,
—C(O)(CH$_2$)$_q$NR$^i$R$^{ii}$,
—C(O)O—C$_{1-12}$-alkyl, wherein alkyl is unsubstituted or substituted with one or more OH, halo, cyano or C$_{1-12}$-alkoxyl,
—S(O)$_2$—C$_{1-12}$-alkyl, or
—S(O)$_2$NR$^i$R$^{ii}$;
R$^i$ and R$^{ii}$ are each independently H or C$_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B;
A is halo, cyano, OH, C$_{1-7}$-alkyl, halo-C$_{1-7}$-alkyl, or C$_{1-7}$-alkoxy;
B is oxo, halo, OH, C$_{1-7}$-alkyl or C$_{1-7}$-alkoxy;
R$^3$ is Cl or F;
n is 1 or 2;
m is 0, 1, 2, 3 or 4;
p is 0, 1 or 2;
q is 1, 2, 3 or 4; and
r is 2, 3 or 4,
or a pharmaceutically acceptable salt thereof.

2. The compound of claim 1, wherein
X—Y is C(R$^a$R$^b$)—O, wherein R$^a$ and R$^b$ are each independently H or methyl,
CH$_2$—S(O)$_p$, wherein p is 0 or 2,
C(O)O,
CH$_2$OCH$_2$, or
CH$_2$CH$_2$O,
Z is CH or N, and
n is 1 or 2.

3. The compound of claim 1, wherein Z is CH.
4. The compound of claim 1, wherein Z is N.
5. The compound of claim 1, wherein n is 1.
6. The compound of claim 1, wherein n is 2.
7. The compound of claim 1, wherein X—Y is CH$_2$—O—, C(H,Me)—O—, or CH$_2$OCH$_2$.
8. The compound of claim 1, wherein R$^1$ is halo.
9. The compound of claim 1, wherein R$^1$ is F.
10. The compound of claim 1, wherein m is 0.
11. The compound of claim 1, wherein m is 1.
12. The compound of claim 1, wherein
R$^2$ is H,
C$_{1-7}$-alkyl, unsubstituted or substituted with one or more OH,
—CH$_2$-pyridinyl,
—C(O)—C$_{1-7}$-alkyl,
—C(O)CH$_2$NR$^i$R$^{ii}$, wherein R$^i$ and R$^{ii}$ are each independently selected from C$_{1-7}$-alkyl,
—C(O)O—C$_{1-4}$-alkyl, or
—S(O)$_2$NR$^i$R$^{ii}$, wherein R$^i$ and R$^{ii}$ are each independently selected from C$_{1-7}$-alkyl.

13. The compound of claim 1, wherein R$^2$ is H, hydroxyethyl, i-propyl, methoxycarbonyl, methyl, methylcarbonyl, N,N-dimethylamino-methyl-carbonyl, N,N-dimethylamino-sulfonyl, pyridin-2-yl-methyl or t-butoxycarbonyl.

14. The compound of claim 1, wherein $R^2$ is $C_{1-7}$-alkyl.

15. The compound of claim 1, wherein $R^2$ is methyl or i-propyl.

16. The compound of claim 1, wherein $R^3$ is Cl.

17. The compound of claim 1, wherein the compound is selected from
- tert-butyl 8-chloro-1-[(1r,4'r)-3H-spiro[2-benzofuran-1,1'-cyclohexan]-4'-yl]-4H-[1,2,4]triazolo[4,3-a][1,4]benzodiazepine-5(6H)-carboxylate;
- 8-chloro-1-[(1r,4'r)-3H-spiro[2-benzofuran-1,1'-cyclohexan]-4'-yl]5,6-dihydro-4H-[1,2,4]triazolo[4,3-a][1,4]benzodiazepine hydrochloride;
- 8-chloro-5-methyl-1-[(1r,4'r)-3H-spiro[2-benzofuran-1,1'-cyclohexan]-4'-yl]-5,6-dihydro-4H-[1,2,4]triazolo[4,3-a][1,4]benzodiazepine;
- tert-butyl 8-chloro-1-[(1s,4's)-3H-spiro[2-benzofuran-1,1'-cyclohexan]-4'-yl]-4H-[1,2,4]triazolo[4,3-a][1,4]benzodiazepine-5(6H)-carboxylate;
- 8-chloro-1-[(1s,4's)-3H-spiro[2-benzofuran-1,1'-cyclohexan]-4'-yl]-5,6-dihydro-4H-[1,2,4]triazolo[4,3-a][1,4]benzodiazepine hydrochloride;
- 8-chloro-5-methyl-1-[(1s,4's)-3H-1-spiro[2-benzofuran-1,1'-cyclohexan]-4'-yl]-5,6-dihydro-4H-[1,2,4]triazolo[4,3-a][1,4]benzodiazepine;
- tert-butyl 8-chloro-1-(1'H,3H-spiro[2-benzofuran-1,4'-piperidin]-1'-yl)-4H-[1,2,4]triazolo[4,3-a][1,4]benzodiazepine-5 (6H)-carboxylate;
- 8-chloro-1-(1'H,3H-spiro[2-benzofuran-1,4'-piperidin]-1'-yl)-5,6-dihydro-4H-[1,2,4]triazolo[4,3-a][1,4]benzodiazepine hydrochloride; and
- 8-chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine.

18. The compound of claim 1, wherein the compound is selected from
- 8-chloro-5-isopropyl-1-(1'H,3H-spiro[2-benzofuran-1,4'-piperidin]-1'-yl)-5,6-dihydro-4H-[1,2,4]triazolo[4,3-a][1,4]benzodiazepine;
- 2-[8-chloro-1-(1'H-3H-spiro[2-benzofuran-1,4'-piperidin]-1'-yl)-4H-[1,2,4]triazolo[4,3-a][1,4]benzodiazepin-5(6H)-yl]ethanol;
- 8-chloro-5-(pyridin-2-ylmethyl)-1-(1'H,3H-spiro[2-benzofuran-1,4'-piperidin]-1'-yl)-5,6-dihydro-4H-[1,2,4]triazolo[4,3-a][1,4]benzodiazepine;
- 8-chloro-N,N-dimethyl-1-(1'H,3H-spiro[2-benzofuran-1,4'-piperidin]-1'-yl)-4H-[1,2,4]triazolo[4,3-a][1,4]benzodiazepine-5(6H)-sulfonamide;
- methyl 8-chloro-1-(1'H,3H-spiro[2-benzofuran-1,4'-piperidin]-1'-yl)-4H-[1,2,4]triazolo[4,3-a][1,4]benzodiazepine-5(6-H)-carboxylate;
- 5-acetyl-8-chloro-1-(1'H,3H-spiro[2-benzofuran-1,4'-piperidin]-1'-yl)-5,6-dihydro-4H-[1,2,4]triazolo[4,3-a][1,4]benzodiazepine;
- 2-[8-chloro-1-(1'H,3H-spiro[2-benzofuran-1,4'-piperidin]-1'-yl)-4H-[1,2,4]triazolo[4,3-a][1,4]benzodiazepin-5(6H)-yl]-N,N-dimethyl-2-oxoethanamine;
- tert-butyl 8-chloro-1-(6-fluoro-1'H,3H-spiro[2-benzofuran-1,4'-piperidin]-1'-yl)-4H-[1,2,4]triazolo[4,3-a][1,4]benzodiazepine-5(6H)-carboxylate; and
- 8-chloro-1-(6-fluoro-1'H,3H-spiro[2-benzofuran-1,4'-piperidin]-1'-yl)-5,6-dihydro-4H-[1,2,4]triazolo[4,3-a][1,4]benzodiazepine hydrochloride.

19. The compound of claim 1, wherein the compound is selected from
- 8-chloro-1-(6-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;
- tert-butyl 8-chloro-1-(7-fluoro-1'H,3H-spiro[2-benzofuran-1,4'-piperidin]-1'-yl)-4H-[1,2,4]triazolo[4,3-a][1,4]benzodiazepine-5(6H)-carboxylate;
- 8-chloro-1-(7-fluoro-1'H,3H-spiro[2-benzofuran-1,4'-piperidin]-1'-yl)-5,6-dihydro-4H-[1,2,4]triazolo[4,3-a][1,4]benzodiazepine hydrochloride;
- 8-chloro-1-(7-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;
- 8-chloro-1-(5-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine;
- tert-butyl 8-chloro-1-(3-methyl-1'H-3H-spiro[2-benzofuran-1,4'-piperidin]-1'-yl)-4H-[1,2,4]triazolo[4,3-a][1,4]benzodiazepine-5(6H)-carboxylate;
- 8-chloro-1-(3-methyl-1'H-3H-spiro[2-benzofuran-1,4'-piperidin]-1'-yl)-5,6-dihydro-4H-[1,2,4]triazolo[4,3-a][1,4]benzodiazepine hydrochloride;
- 8-chloro-5-methyl-1-(3-methyl-1'H-3H-spiro[2-benzofuran-1,4'-piperidin]-1'-yl)-5,6-dihydro-4H-[1,2,4]triazolo[4,3-a][1,4]benzodiazepine;
- 1'-(8-chloro-5-methyl-5,6-dihydro-4H-[1,2,4]triazolo[4,3-a][1,4]benzodiazepin-1-yl)-3H-spiro[2-benzofuran-1,4'-piperidin]-3-one; and
- 8-chloro-1-(1'H,3H-spiro[2-benzothiophene-1,4'-piperidin]-1'-yl)-5,6-dihydro-4H-[1,2,4]triazolo[4,3-a][1,4]benzodiazepine.

20. The compound of claim 1, wherein the compound is selected from
- 8-chloro-5-methyl-1-(1'H,3H-spiro[2-benzothiophene-1,4'-piperidin]-1'-yl)-5,6-dihydro-4H-[1,2,4]triazolo[4,3-a][1,4]benzodiazepine;
- 8-chloro-1-(2,2-dioxido-1'H,3H-spiro[2-benzothiophene-1,4'-piperidin]-1'-yl)-5,6-dihydro-4H-[1,2,4]triazolo[4,3-a][1,4]benzodiazepine;
- 8-chloro-1-(2,2-dioxido-1'H,3H-spiro[2-benzothiophene-1,4'-piperidin]-1'-yl)-5-methyl-5,6-dihydro-4H-[1,2,4]triazolo[4,3-a][1,4]benzodiazepine;
- 1'-(8-chloro-5-methyl-5,6-dihydro-4H-[1,2,4]triazolo[4,3-a][1,4]benzodiazepin-1-yl)-1H-spiro[isochromene-4,4'-piperidine];
- tert-butyl 8-chloro-1-(3,4-dihydro-1'H-spiro[isochromene-1,4'-piperidin]-1'-yl)-4H-[1,2,4]triazolo[4,3-a][1,4]benzodiazepine-5(6H)-carboxylate;
- 1'-(8-chloro-5,6-dihydro-4H-[1,2,4]triazolo[4,3-a][1,4]benzodiazepin-1-yl)-3,4-dihydrospiro[isochromene-1,4'-piperidine]hydrochloride;
- 1'-(8-chloro-5-methyl-5,6-dihydro-4H-[1,2,4]triazolo[4,3-a][1,4]benzodiazepin-1-yl)-3,4-dihydrospiro[isochromene-1,4'-piperidine];
- (+)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran]; and
- (−)-1-(8-chloro-5-methyl-5,6-dihydro-4H-1-[1,2,4]triazolo[4,3-a][1,4]benzodiazepin-1-yl)-3'H-spiro[azepane-4,1'-[2]benzofuran].

21. The compound of claim 1, wherein the compound is selected from
- (+)-1-(8-chloro-5-methyl-5,6-dihydro-4H-[1,2,4]triazolo[4,3-a][1,4]benzodiazepin-1-yl)-3'H-spiro[azepane-4,1'[2]benzofuran],
- 8-chloro-5-methyl-1-[(1r,4'r)-3H-spiro[2-benzofuran-1,1'-cyclohexan]-4'-yl]-5,6-dihydro-4H-[1,2,4]triazolo[4,3-a][1,4]benzodiazepine, 8-chloro-5-methyl-1-(3-methyl-1'H,3H-spiro[2-benzofuran-1,4'-piperidin]-1'-yl)-5,6-dihydro-4H-[1,2,4]triazolo[4,3-a][1,4]benzodiazepine, (−)-1-(8-chloro-5-methyl-5,6-dihydro-4H-[1,2,4]triazolo[4,3-a][1,4]benzodiazepin-1-yl)-3'H-spiro[azepane-4,1'-[2]benzofuran], 8-chloro-5-methyl-1-(1'H,3H-spiro[2-benzofuran-1,4'-piperidin]-1'-yl)-5,6-dihydro-4H-[1,2,4]triazolo[4,3-a][1,4]benzodiazepine, 1'-(8-chloro-5-methyl-5,6-dihydro-1H-[1,2,4]triazolo[4,3-a][1,4]benzodiazepin-1-yl)-1H-spiro[isochromene-4,4'-piperidine], 8-chloro-1-(6-fluoro-1'H-1,3H-spiro[2-benzofuran-1,4'-piperidin]-1'-yl)-5-methyl-5,6-dihydro-4H-[1,2,4]triazolo[4,3-a][1,4]benzodiazepine, 8-chloro-5-isopropyl-1-(1'H,3H-spiro[2-benzofuran-1,4'-piperidin]-1'-yl)-5,6-dihydro-4H-[1,2,4]triazolo[4,3-a][1,4]benzodiazepine, and 8-chloro-1-(5-fluoro-1'H,3H-spiro[2-benzofuran-1,4'-piperidin]-1'-yl)-5-methyl-5,6-dihydro-4H-[1,2,4]triazolo[4,3-a][1,4]benzodiazepine.

22. A pharmaceutical composition comprising a therapeutically effective amount of a compound of formula I

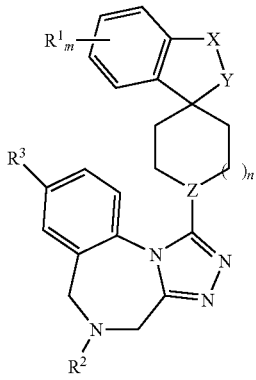

wherein

X—Y is $C(R^aR^b)$—O, wherein $R^a$ and $R^b$ are each independently H or $C_{1-4}$-alkyl, $C(R^cR^d)$—$S(O)_p$, wherein $R^c$ and $R^d$ are each independently H or $C_{1-4}$-alkyl,

C(O)O, $CH_2OCH_2$, or $CH_2CH_2O$;

Z is CH or N;

$R^1$ is halo, cyano, $C_{1-4}$-alkoxy, or $C_{1-4}$-alkyl;

$R^2$ is H, $C_{1-12}$-alkyl, unsubstituted or substituted with one or more OH, halo, cyano or $C_{1-12}$-alkoxy, —$(CH_2)_q$—$R^e$, wherein $R^e$ is phenyl or 5- or 6-membered heteroaryl, each unsubstituted or substituted with one or more substituents independently selected from A, —$(CH_2)_rNR^iR^{ii}$, —C(O)—$C_{1-12}$-alkyl, wherein $C_{1-12}$-alkyl is unsubstituted or substituted with one or more OH, halo, cyano or $C_{1-12}$-alkoxy, —$C(O)(CH_2)_qOC(O)$—$C_{1-12}$-alkyl, —$C(O)(CH_2)_qNR^iR^{ii}$, —C(O)O—$C_{1-12}$-alkyl, wherein alkyl is unsubstituted or substituted with one or more OH, halo, cyano or $C_{1-12}$-alkoxy, —$S(O)_2$—$C_{1-12}$-alkyl, or —$S(O)_2NR^iR^{ii}$;

$R^i$ and $R^{ii}$ are each independently H or $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B;

A is halo, cyano, OH, $C_{1-7}$-alkyl, halo-$C_{1-7}$-alkyl, or $C_{1-7}$-alkoxy;

B is oxo, halo, OH, $C_{1-7}$-alkyl or $C_{1-7}$-alkoxy;

$R^3$ is Cl or F;

n is 1 or 2;

m is 0, 1, 2, 3 or 4;

p is 0, 1 or 2;

q is 1, 2, 3 or 4; and r is 2, 3 or 4, or a pharmaceutically acceptable salt thereof and a pharmaceutically acceptable carrier.

* * * * *